(12) United States Patent
Socolovsky et al.

(10) Patent No.: US 11,661,581 B2
(45) Date of Patent: May 30, 2023

(54) USE OF CDK INHIBITORS TO ENHANCE GROWTH AND SELF-RENEWAL OF PROGENITOR CELLS

(71) Applicant: University of Massachusetts, Boston, MA (US)

(72) Inventors: Merav Socolovsky, Brookline, MA (US); Ralph Scully, Brookline, MA (US); Yung Hwang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 253 days.

(21) Appl. No.: 15/988,643

(22) Filed: May 24, 2018

(65) Prior Publication Data

US 2018/0340148 A1    Nov. 29, 2018

Related U.S. Application Data

(60) Provisional application No. 62/510,913, filed on May 25, 2017.

(51) Int. Cl.
| | |
|---|---|
| *A61K 35/18* | (2015.01) |
| *A61K 35/38* | (2015.01) |
| *C12N 5/078* | (2010.01) |
| *C12N 5/0789* | (2010.01) |
| *A61P 7/06* | (2006.01) |

(Continued)

(52) U.S. Cl.
CPC ............ *C12N 5/0641* (2013.01); *A61K 35/18* (2013.01); *A61K 35/28* (2013.01); *A61K 38/1709* (2013.01); *A61P 7/06* (2018.01); *C12N 5/0647* (2013.01); *C12N 2501/105* (2013.01); *C12N 2501/14* (2013.01); *C12N 2501/22* (2013.01); *C12N 2501/2303* (2013.01); *C12N 2501/2306* (2013.01); *C12N 2501/26* (2013.01); *C12N 2501/39* (2013.01); *C12N 2501/405* (2013.01); *C12N 2501/998* (2013.01)

(58) Field of Classification Search
CPC ................ C12N 5/0641; C12N 5/0647; C12N 2501/105; C12N 2501/14; C12N 2501/22; C12N 2501/2303; C12N 2501/2306; C12N 2501/26; C12N 2501/39; C12N 2501/405; C12N 2501/998; A61P 7/06; A61K 35/18; A61K 35/28; A61K 38/1709; A61K 35/1709
See application file for complete search history.

(56) References Cited

U.S. PATENT DOCUMENTS

| | | | |
|---|---|---|---|
| 2003/0069430 A1* | 4/2003 | Davis | A61P 9/10 546/277.7 |
| 2005/0075499 A1* | 4/2005 | Benedict | A61P 29/00 540/488 |

(Continued)

OTHER PUBLICATIONS

Song et al., "Effect of the Cdk-inhibitor roscovitine on mouse hematopoietic progenitors in vivo and in vitro", 2007, Cancer Chemotherapy and Pharmacology 60, p. 841-849.*

(Continued)

*Primary Examiner* — Kevin K Hill
(74) *Attorney, Agent, or Firm* — Fish & Richardson P.C.

(57) ABSTRACT

Methods for using cyclin-dependent kinase (CDK) inhibitors to enhance growth and self-renewal of progenitor cells, in vitro and in vivo.

6 Claims, 19 Drawing Sheets
(17 of 19 Drawing Sheet(s) Filed in Color)
Specification includes a Sequence Listing.

(51) Int. Cl.
A61K 38/17 (2006.01)
A61K 35/28 (2015.01)

(56) References Cited

U.S. PATENT DOCUMENTS

2013/0059783 A1* 3/2013 Flygare ............... C12N 5/0641
514/13.5
2016/0068810 A1* 3/2016 Palis ................... C12N 5/0641
424/93.73

OTHER PUBLICATIONS

Panzenbock et al., "Growth and Differentiation of Human Stem Cell Factor/Erythropoietin-Dependent Erythroid Progenitor Cells In Vitro", 1998, Blood 92(10), p. 3658-3668.*
Sonoda et al., "Synergistic Actions of Stem Cell Factor and Other Burst-Promoting Activities on Proliferation of CD34' Highly Purified Blood Progenitors Expressing HLA-DR or Different Levels of c-kit Protein", 1994, Blood 84(12), p. 4099-4106.*
Cicenas et al., "Highlights of the Latest Advances in Research on CDK Inhibitors", Oct. 27, 2014, Cancers 6, p. 2224-2242.*
Correll et al, Truncating the Y-Axis, arXiv: 1907.02035v2, Jan. 8, 2020.*
Liang et al, J. Enzyme Inhibition and Medicinal Chemistry 35(1): 235-244, 2020.*
Hofmann et al, Oncogene 20: 4198-4208, 2001.*
Vita, Thesis, Preclinical Studies of Roscovitine, Department of Medicine, Division of Hematology, Karolinska Univeristy Hospital, Huddinge Karolinska Institute, Sweden, 2005; cover pages (1-2) and excerpted portion only (p. 41); 3 pages total.*
Hassan et al, SQU Med. J. 11(2): 165-178, 2011.*
Ambros, "Cell cycle-dependent sequencing of cell fate decisions in Caenorhabditis elegans vulva precursor cells," Development, 1999, 126: 1947-1956.
Aparicio and Gottschling, "Overcoming telomeric silencing: a trans-activator competes to establish gene expression in a cell cycle-dependent way," Genes Dev, 1994, 8: 1133-1146.
Bauer et al., "The glucocorticoid receptor is required for stress erythropoiesis," Genes Dev, 1999, 13: 2996-3002.
Bensimon et al., "Alignment and sensitive detection of DNA by a moving interface," Science, 1994, 265: 2096-2098.
Besson et al., "CDK inhibitors: cell cycle regulators and beyond," Dev Cell, 2008, 14: 159-169.
Bianco et al., "Analysis of DNA replication profiles in budding yeast and mammalian cells using DNA combing," Methods, 2012, 57: 149-157.
Bird et al., "Helper T Cell Differentiation Is Controlled by the Cell Cycle," Immunity, 1998, 9: 229-237.
Cai et al., "In search of 'stemness'," Exp Hematol, 2004, 32: 585-598.
Cantor and Orkin, "Transcriptional regulation of erythropoiesis: an affair involving multiple partners," Oncogene, 2002, 21: 3368-3376.
Chiu and Blau, "Reprogramming cell differentiation in the absence of DNA synthesis," Cell, 1984, 37: 879-887.
Conti et al., "The Mammalian DNA Replication Elongation Checkpoint: Implication of Chk1 and Relationship with Origin Firing as Determined by Single DNA Molecule and Single Cell Analyses," Cell Cycle, 2007, 6: 2760-2767.
Dahlberg et al., "Ex vivo expansion of human hematopoietic stem and progenitor cells," Blood, Jun. 2011, 117: 6083-6090.
Dalton and Coverdell, "Linking the Cell Cycle to Cell Fate Decisions," Trends Cell Biol, 2015, 25: 592-600.
De Nooij and Hariharan, "Uncoupling cell fate determination from patterned cell division in the Drosophila eye," Science, 1995, 270: 983-985.
Dolznig et al., Expansion and Differentiation of Immature Mouse and Human Hematopoietic Progenitors, Methods in Molecular Medicine, 2005, 105: 323-343.

Douay and Andreu, "Ex vivo Production of Human Red Blood Cells From Hematopoietic Stem Cells: What Is the Future in Transfusion?," Transfusion Medicine Reviews, Apr. 2007, 21: 91-10.
Duronio, "Developing S-phase control," Genes Dev, 2012, 26: 746-750.
Edgar and McGhee, "DNA synthesis and the control of embryonic gene expression in C. elegans," Cell, 1988, 53: 589-599.
Edgar and O'Farrell, "The three postblastoderm cell cycles of Drosophila embryogenesis are regulated in G2 by string," Cell, 1990, 62: 469-480.
England et al., "Immature erythroblasts with extensive ex vivo self-renewal capacity emerge from the early mammalian fetus," Blood, 2011, 117: 2708-2717.
Farrell, "Embryonic onset of late replication requires Cdc25 downregulation," Genes Dev, 2012, 26: 714-725.
Fisher and Mechali, "Vertebrate HoxB gene expression requires DNA replication," Embo J, 2003, 22: 3737-3748.
Flores-Guzman et al., "Concise Review: Ex Vivo Expansion of Cord Blood-Derived Hematopoietic Stem and Progenitor Cells: Basic Principles, Experimental Approaches, and Impact in Regenerative Medicine," Stem Cells Translational Medicine, 2013, 2: 830-838.
Flores-Rozas et al., "Cdk-interacting protein 1 directly binds with proliferating cell nuclear antigen and inhibits DNA replication catalyzed by the DNA polymerase delta holoenzyme," PNAS, 1994, 91: 8655-8659.
Flygare et al., "HIF1alpha synergizes with glucocorticoids to promote BFU-E progenitor self-renewal," Blood, 2011, 117: 3435-3444.
Foe, "Mitotic domains reveal early commitment of cells in Drosophila embryos," Development, 1989, 107: 1-22.
Forlani et al., "Relief of a repressed gene expression state in the mouse 1-cell embryo requires DNA replication," Development, 1998, 125: 3153-3166.
Ge et al., "Dormant origins licensed by excess Mcm2-7 are required for human cells to survive replicative stress," Genes Dev, 2007, 21: 3331-3341.
Giarratana et al., "Proof of principle for transfusion of in vitro-generated red blood cells," Blood, Nov. 2011, 118: 5071-5079.
Gitlin et al., "T cell help controls the speed of the cell cycle in germinal center B cells," Science, 2015, 349: 643-646.
Gonzales et al., "Deterministic Restriction on Pluripotent State Dissolution by Cell-Cycle Pathways," Cell, 2015, 162: 564-579.
Goren and Cedar, "Replicating by the clock," Nat Rev Mol Cell Biol, 2003, 4: 25-32.
Gregory et al., "Erythropoietic progenitors capable of colony formation in culture: response of normal and genetically anemic W-W-V mice to manipulations of the erythron," J Cell Physiol, 1974, 84: 1-12.
Gu et al., "Interaction of myogenic factors and the retinoblastoma protein mediates muscle cell commitment and differentiation," Cell, 1993, 72: 309-324.
Hanahan and Weinberg, "The Hallmarks of Cancer," Cell, 2000, 100(1):57-70.
Hansen et al., "Sequencing newly replicated DNA reveals widespread plasticity in human replication timing," PNAS, 2010, 107: 139-144.
Hara and Ogawa, "Erythropoietic precursors in mice with phenylhydrazine-induced anemia," Am J Hematol, 1976, 1: 453-458.
Harris and Hartenstein, "Neuronal determination without cell division in Xenopus embryos," Neuron, 1991, 6: 499-515.
Hartenstein and Posakony, "Sensillum development in the absence of cell division: the sensillum phenotype of the Drosophila mutant string," Dev Biol, 1990, 138: 147-158.
Hashimoto et al., "Critical role for the 310 helix region of p57(Kip2) in cyclin-dependent kinase 2 inhibition and growth suppression," J Biol Chem, 1998, 273: 16544-16550.
Henikoff, "Nucleosome destabilization in the epigenetic regulation of gene expression," Nat Rev Genet, 2008, 9: 15-26.
Hiratani et al., "Replication timing and transcriptional control: beyond cause and effect—part II," Curr Opin Genet Dev, 2009, 19: 142-149.

(56) References Cited

OTHER PUBLICATIONS

Jones and Petermann, "Replication fork dynamics and the DNA damage response," Biochemical Journal, 2012, 443: 13-26.
Knapp et al., "Dissociation of Survival, Proliferation, and State Control in Human Hematopoietic Stem Cells," Stem Cell Reports, Jan. 2017, 8: 152-162.
Koulnis et al., "Identification and Analysis of Mouse Erythroid Progenitors using the CD71/TER119 Flow-cytometric Assay," J Vis Exp, 2011.
Lam et al., "Analysis of germline CDKN1C (p57KIP2) mutations in familial and sporadic Beckwith-Wiedemann syndrome (BWS) provides a novel genotype-phenotype correlation," Journal of Medical Genetics, 1999, 36: 518-523.
Lee et al., "Cloning of p57KIP2, a cyclin-dependent kinase inhibitor with unique domain structure and tissue distribution," Genes Dev, 1995, 9: 639-649.
Lee et al., "PPAR-[agr] and glucocorticoid receptor synergize to promote erythroid progenitor self-renewal," Nature, 2015, 522: 474-477.
Lim and Kaldis, "Cdks, cyclins and CKIs: roles beyond cell cycle regulation," Development, 2013, 140(15):3079-3093.
Loog et al., "Cyclin specificity in the phosphorylation of cyclin-dependent kinase substrates," Nature. 2005;434(7029):104-108.
Mac Auley et al., "Characterization of the unusually rapid cell cycles during rat gastrulation," Development, 1993, 117: 873-883.
Mariaule and Belmont, "Cyclin-Dependent Kinase Inhibitors as Marketed Anticancer Drugs: Where Are We Now? A Short Survey," Molecules, 2014, 19:14346-14382.
Martynoga et al., "Foxg1 is required for specification of ventral telencephalon and region-specific regulation of dorsal telencephalic precursor proliferation and apoptosis," Dev Biol, 2005, 283: 113-127.
Matsumoto et al., "p57 is required for quiescence and maintenance of adult hematopoietic stem cells," Cell Stem Cell, 2011, 9: 262-271.
Matsuoka et al., "p57KIP2, a structurally distinct member of the p21CIP1 Cdk inhibitor family, is a candidate tumor suppressor gene," Genes Dev, 1995, 9: 650-662.
McKnight and Miller, Jr., "Electron microscopic analysis of chromatin replication in the cellular blastoderm *Drosophila melanogaster* embryo," Cell, 1977, 12: 795-804.
Meijer et al., "Biochemical and Cellular Effects of Roscovitine, a Potent and Selective Inhibitor of the Cyclin-Dependent Kinases cdc2, cdk2 and cdk5," European Journal of Biochemistry, 1997, 243: 527-536.
Migliaccio et al., "In vitro mass production of human erythroid cells from the blood of normal donors and of thalassemic patients," Blood Cells Mol Dis, 2002, 28: 169-180.
Migliaccio et al., "The potential of stem cells as an in vitro source of red blood cells for transfusion," Cell Stem Cell, 2012, 10: 115-119.
Migliaccio et al., "The Potential of Stem Cells as an In Vitro Source of Red Blood Cells for Transfusion," Cell Stem Cell, Feb. 2012, 10: 115-119.
Miller and Nasmyth, "Role of DNA replication in the repression of silent mating type loci in yeast," Nature, 1984, 312: 247-251.
Monette et al., "Erythropoiesis in the rat: differential rates of DNA synthesis and cell proliferation," Science, 1968, 162: 1132-1134.
Nordman and Orr-Weaver, "Regulation of DNA replication during development," Development, 2012, 139: 455-464.
Nyberg et al., "Toward Maintaining the Genome: DNA Damage and Replication Checkpoints," Annual Review of Genetics, 2002, 36: 617-656.
O'Farrell et al., "Embryonic cleavage cycles: how is a mouse like a fly?," Curr Biol, 2004, 14: R35-45.
Pateras et al., "p57KIP2: 'Kip'ing the cell under control," Mol Cancer Res, 2009, 7: 1902-1919.
Pop et al., "A key commitment step in erythropoiesis is synchronized with the cell cycle clock through mutual inhibition between PU.1 and S-phase progression," PLoS Biol, 2010, 8: e1000484.

Romanelli et al., "CDKN1C (p57Kip2) analysis in Beckwith-Wiedemann syndrome (BWS) patients: Genotype-phenotype correlations, novel mutations, and polymorphisms," American Journal of Medical Genetics Part A, 2010, 152A: 1390-1397.
Santo et al., "Targeting Cyclin-Dependent Kinases and Cell Cycle Progression in Human Cancers," Semin Oncol, 2015, 42(6):788-800.
Scadden and Srivastava, "Advancing Stem Cell Biology toward Stem Cell Therapeutics," Cell Stem Cell, Feb. 2012, 10: 149-150.
Scully et al., "Dynamic changes of BRCA1 subnuclear location and phosphorylation state are initiated by DNA damage," Cell, 1997, 90: 425-435.
Shearstone et al., "Global DNA demethylation during mouse erythropoiesis in vivo," Science, 2011, 334: 799-802.
Snow and Bennett, "Gastrulation in the mouse: assessment of cell populations in the epiblast of tw18/tw18 embryos," J Embryol Exp Morphol, 1978, 47: 39-52.
Socolovsky et al., "Ineffective erythropoiesis in Stat5a(−/−)5b(−/−) mice due to decreased survival of early erythroblasts," Blood, 2001, 98: 3261-3273.
Spradling and Orr-Weaver, "Regulation of DNA replication during *Drosophila* development," Annu Rev Genet, 1987, 21: 373-403.
Tanaka et al., "CDK-dependent phosphorylation of Sld2 and Sld3 initiates DNA replication in budding yeast," Nature, 2007, 445: 328-332.
Vlach et al., "Phosphorylation-dependent degradation of the cyclin-dependent kinase inhibitor p27," EMBO J, 1997, 16: 5334-5344.
Von Lindern et al., "Control of erythropoiesis by erythropoietin and stem cell factor: a novel role for Bruton's tyrosine kinase," Cell Cycle, 2004, 3: 876-879.
Von Lindern et al., "The glucocorticoid receptor cooperates with the erythropoietin receptor and c-Kit to enhance and sustain proliferation of erythroid progenitors in vitro," Blood, 1999, 94: 550-559.
Waga et al., "Differential effects by the p21 CDK inhibitor on PCNA-dependent DNA replication and repair," Nature, 1994, 371: 534-537.
Waga et al., "The p21 inhibitor of cyclin-dependent kinases controls DNA replication by interaction with PCNA," Nature, 1994, 369: 574-578.
Watanabe et al., "Suppression of cell transformation by the cyclin-dependent kinase inhibitor p57KIP2 requires binding to proliferating cell nuclear antigen," PNAS, 1998, 95: 1392-1397.
Weigmann and Lehner, "Cell fate specification by even-skipped expression in the *Drosophila* nervous system is coupled to cell cycle progression," Development, 1995, 121: 3713-3721.
Weinberg, "The Retinoblastoma Protein and Cell Cycle Control," Cell, 1995, 81(3):323-330.
Weintraub, "Assembly of an active chromatin structure during replication," Nucleic Acids Res, 1979, 7: 781-792.
Wognum et al., "Hematopoietic Stem and Progenitor Cells," StemCell Technologies, 2015, 10 pages.
Wolffe, "Implications of DNA replication for eukaryotic gene expression," J Cell Sci, 1991, 99 ( Pt 2): 201-206.
Wontakal et al., "A core erythroid transcriptional network is repressed by a master regulator of myelo-lymphoid differentiation," PNAS, 2012, 109: 3832-3837.
Yan et al., "Ablation of the CDK inhibitor p57Kip2 results in increased apoptosis and delayed differentiation during mouse development," Genes Dev, 1997, 11: 973-983.
Yokota et al., "Markers for Hematopoietic Stem Cells: Histories and Recent Achievements," Advances in Hematopoietic Stem Cell Research, 2012, 77-88.
Zegerman and Diffley, "Phosphorylation of Sld2 and Sld3 by cyclin-dependent kinases promotes DNA replication in budding yeast," Nature, 2007, 445: 281-285.
Zeman and Cimprich, "Causes and consequences of replication stress," Nat Cell Biol, 2014, 16: 2-9.
Zhang et al., "Altered cell differentiation and proliferation in mice lacking p57KIP2 indicates a role in Beckwith-Wiedemann syndrome," Nature, 1997, 387: 151-158.
Zhang et al., "Role of Ras signaling in erythroid differentiation of mouse fetal liver cells: functional analysis by a flow cytometry-based novel culture system," Blood, 2003, 102: 3938-3946.

(56) References Cited

OTHER PUBLICATIONS

Zhang et al., "ZFP36L2 is required for self-renewal of early burst-forming unit erythroid progenitors," Nature, 2013, 499: 92-96.
Zhu and Skoultchi, "Coordinating cell proliferation and differentiation," Curr Opin Genet Dev, 2001, 11: 91-97.
Zou et al., "p57(Kip2) and p27(Kip1) cooperate to maintain hematopoietic stem cell quiescence through interactions with Hsc70," Cell Stem Cell, 2011, 9: 247-261.
Hsieh et al., "Repositioning of a cyclin-dependent kinase inhibitor GW8510 as a ribonucleotide reductase M2 inhibitor to treat human colorectal cancer," Cell Death Discovery, May 9, 2016, 2(1):1-8.
Roskoski Jr, "Cyclin-dependent protein kinase inhibitors including palbociclib as anticancer drugs," Pharmacological Research, May 1, 2016, 107:249-75.
Whittaker et al., "Inhibitors of cyclin-dependent kinases as cancer therapeutics," Pharmacology & Therapeutics, May 1, 2017, 173:83-105.
Socolovsky et al., "Control of hematopoietic differentiation: lack of specificity in signaling by cytokine receptors," Proceedings of the National Academy of Sciences, Jun. 9, 1998, 95(12):6573-5.

\* cited by examiner

A
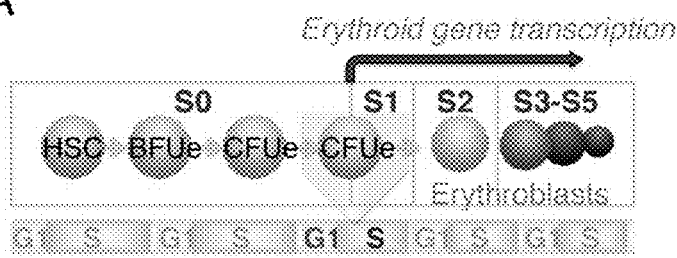
B
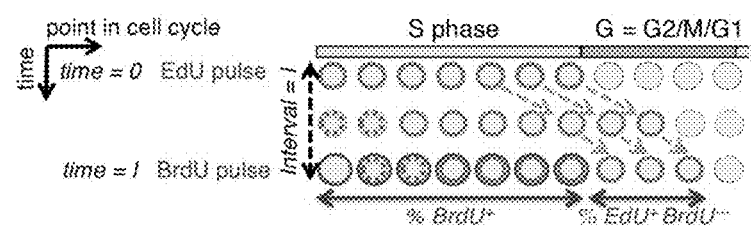
C 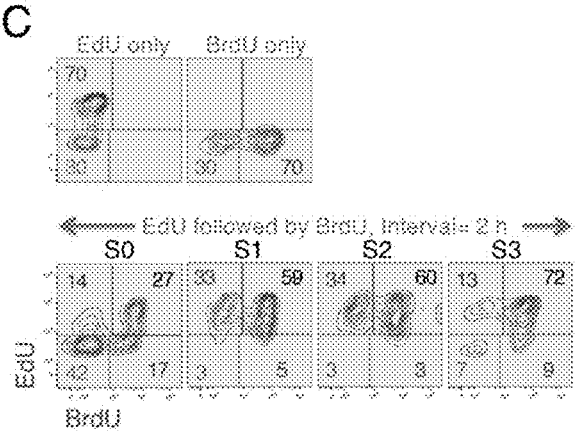 D 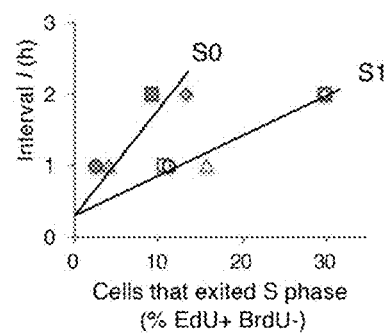
E
| | Total Cycle (h) | S (h) | G1 (h) | G2 & M (h) |
|---|---|---|---|---|
| S0 | 15 ± 0.3 | 7.3 ± 0.3 | 5.7 ± 0.6 | 2.0 ± 0.7 |
| S1 | 5.8 ± 0.1 | 4.1 ± 0.2 | 1.3 ± 0.3 | 0.5 ± 0.1 |
FIGs. 1A-1E

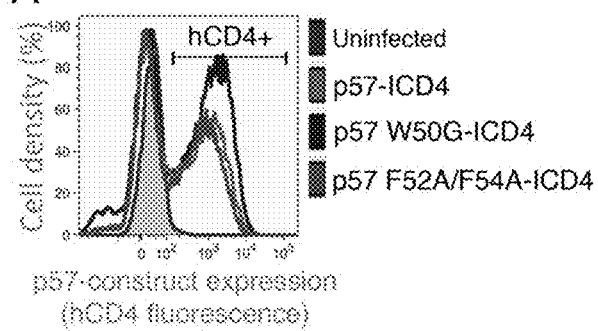
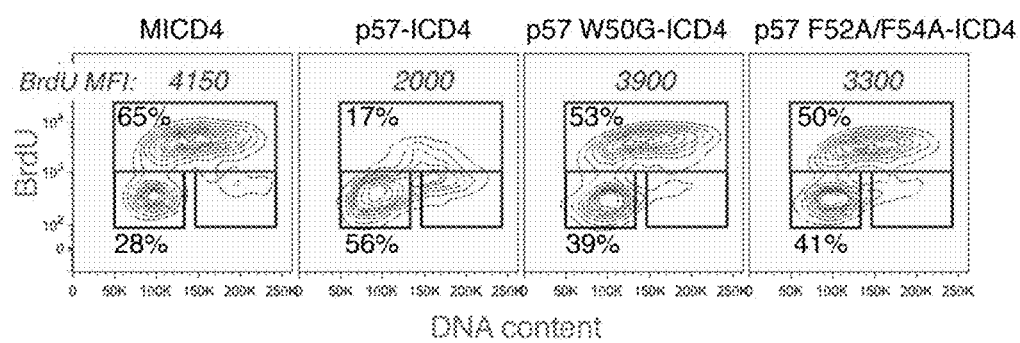
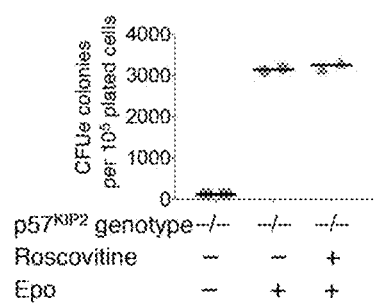
FIGs. 12A-12B

USE OF CDK INHIBITORS TO ENHANCE GROWTH AND SELF-RENEWAL OF PROGENITOR CELLS

CLAIM OF PRIORITY

This application claims priority under 35 USC § 119(e) to U.S. Provisional Patent Application Ser. No. 62/510,913, filed on May 25, 2017. The entire contents of the foregoing are hereby incorporated by reference.

FEDERALLY SPONSORED RESEARCH OR DEVELOPMENT

This invention was made with Government support under Grant Nos. DK099281 and DK100915 awarded by the National Institutes of Health. The Government has certain rights in the invention.

TECHNICAL FIELD

Methods for using cyclin-dependent kinase (CDK) inhibitors to enhance growth and self-renewal of progenitor cells, in vitro and in vivo.

BACKGROUND

The timing and execution of developmental cell fate decisions are incompletely understood. The cell cycle is implicated in such decisions through interactions between cell cycle and transcriptional regulators (1-3) and through cell-cycle phase-specific receptiveness to differentiation cues (4-7). Reconfiguration of lineage-specific chromatin loci, a pre-requisite for the execution of cell fate decisions, was hypothesized to require S phase, since the passage of the replication fork transiently disrupts nucleosomes (8, 9). However, developmental transitions and associated dynamic changes in chromatin are possible in the absence of S phase (10-15). These findings notwithstanding, S phase is essential for activation or silencing of some genes in yeast (16, 17) and for a subset of cell fate decisions in metazoa (18-22), though the precise role and underlying mechanisms linking S phase to these decisions remain unclear.

SUMMARY

Cell cycle regulators are increasingly implicated in cell fate decisions such as the acquisition or loss of pluripotency and self-renewal potential. The cell cycle mechanisms that regulate these cell fate decisions are largely unknown. Here we studied an S phase-dependent cell fate switch, in which murine stem cells, including early erythroid progenitors, transition in vivo from a self-renewal state into a phase of active erythroid gene transcription and concurrent maturational cell divisions. We found that progenitors are dependent on $p57^{KIP2}$-mediated slowing of replication forks for self-renewal, a new function for cyclin-dependent kinase (CDK) inhibitors.

We identified a novel function for the CDKI p57KIP2 during self-renewal of early erythroid progenitors (CFU-e) in vitro and in vivo. p57KIP2 promotes the viability of self-renewing cells by slowing down replication forks during S phase and prolonging S phase, thereby preventing replication stress. In its absence, progenitors fail to self-renew, and undergo cell death, probably as a result of DNA damage and replication stress.

We have also shown that it is possible to rescue self-renewal in p57KIP2-deficient cells, by either transducing them back with p57KIP2, or by treating them with a CDKI drug, roscovitine, whose function is similar to that of the P57KIP2 regulator. It is of interest that roscovitine also promotes the self-renewal of wild-type cells, resulting in 2 fold more progenitors than in its absence, in a period of 7-9 days.

As shown herein, treatment of erythroid, and possibly other progenitors and stem cells, with roscovitine, enhances their self-renewal in vitro and in vivo.

Thus, provided herein are methods for providing a population of early erythroid progenitor cells, e.g., CFU-e cells; the methods include providing a starting population of cells comprising mononuclear cells from cord blood, peripheral blood, bone marrow or other hematopoietic tissues, maintaining the starting population in the presence of a sufficient amount of a Cyclin-Dependent Kinase inhibitor (CDKi) under conditions sufficient for generation and expansion of a desired number of early erythroid progenitor cells. The key components of the media typically include: erythropoietin, stem cell factor, insulin-growth-factor-1 (IGF1), a serum-free medium with supplements (many available commercially) that include lipids, insulin, and/or transferrin. In some embodiments, the starting population has been enriched for CD36+ or Lin− cells, e.g., using FACS or density gradient.

In addition, described herein are methods for treating a subject who has anemia, comprising administering to the subject a therapeutically effective amount of cells produced by a method described herein.

Also provided herein are methods for providing a population of hematopoietic stem cells (HSCs), comprising providing a starting population comprising bone marrow, mobilixed peripheral blood, or umbilical cord blood, and include maintaining the starting population of cells in the presence of a sufficient amount of a Cyclin-Dependent Kinase inhibitor (CDKi) under conditions sufficient for generation and expansion of a desired number of HSCs, e.g., conditions comprising culture in the presence of one or more of five growth factors: SCF, IL-3, IL-6, G-CSF, and Flt3L.

In addition, provided herein are methods for treating a subject who has anemia or a bone marrow failure syndrome (BMFS), comprising administering to a subject in need thereof a therapeutically effective amount of a Cyclin-Dependent Kinase inhibitor (CDKi).

In some embodiments of the methods described herein, the CDKi inhibits CDK1 and/or CDK2. In some embodiments, the CDKi does not inhibit CDK4.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1E. S phase shortening at the transition from self-renewal to differentiation in vivo (1A) Schematic depicting sequential flow-cytometric fetal liver subsets S0 to S5 during erythroid differentiation (see flow cytometric profile in FIG. S1A). Seventy percent of S0 and all of S1 cells have CFUe potential. The transition from S0 to S1 marks a switch from CFUe self-renewal to differentiation. The S0/S1 switch is S phase dependent and takes place in early S phase of the last CFUe generation (23).

(1B) The double deoxynucleoside label approach. Pregnant female mice were injected with EdU at t=0, and with BrdU following a time interval 'I'. Fetal livers were harvested and analyzed shortly after the BrdU pulse. Cells in S phase of the cycle at the time of the EdU pulse incorporate EdU into their DNA, and retain this label as they progress through the cycle (represented as green cells). Cells entering S phase continue to take up EdU during the interval I, until EdU is cleared from the blood (shown as dashed green circles). Similarly, cells that are in S phase during the BrdU pulse become labeled with BrdU (red). The 'green only' cells (EdU$^+$BrdU$^-$) represent cells that were in S phase during the first, EdU pulse, but have exited S phase during the interval I. This cell fraction f is proportional to the length of the interval I, as long as I is shorter than the gap phase (G2+M+G1). By trial and error, we found that, for I to be shorter than the gap phase of S1 cells, it needs to be ≤2 h. The linear relationship between I and f can be expressed in terms of the cell cycle length:

$$I/Tc = f$$

Figures 2A, 2B, 2C, 2D, 2E, 2F:
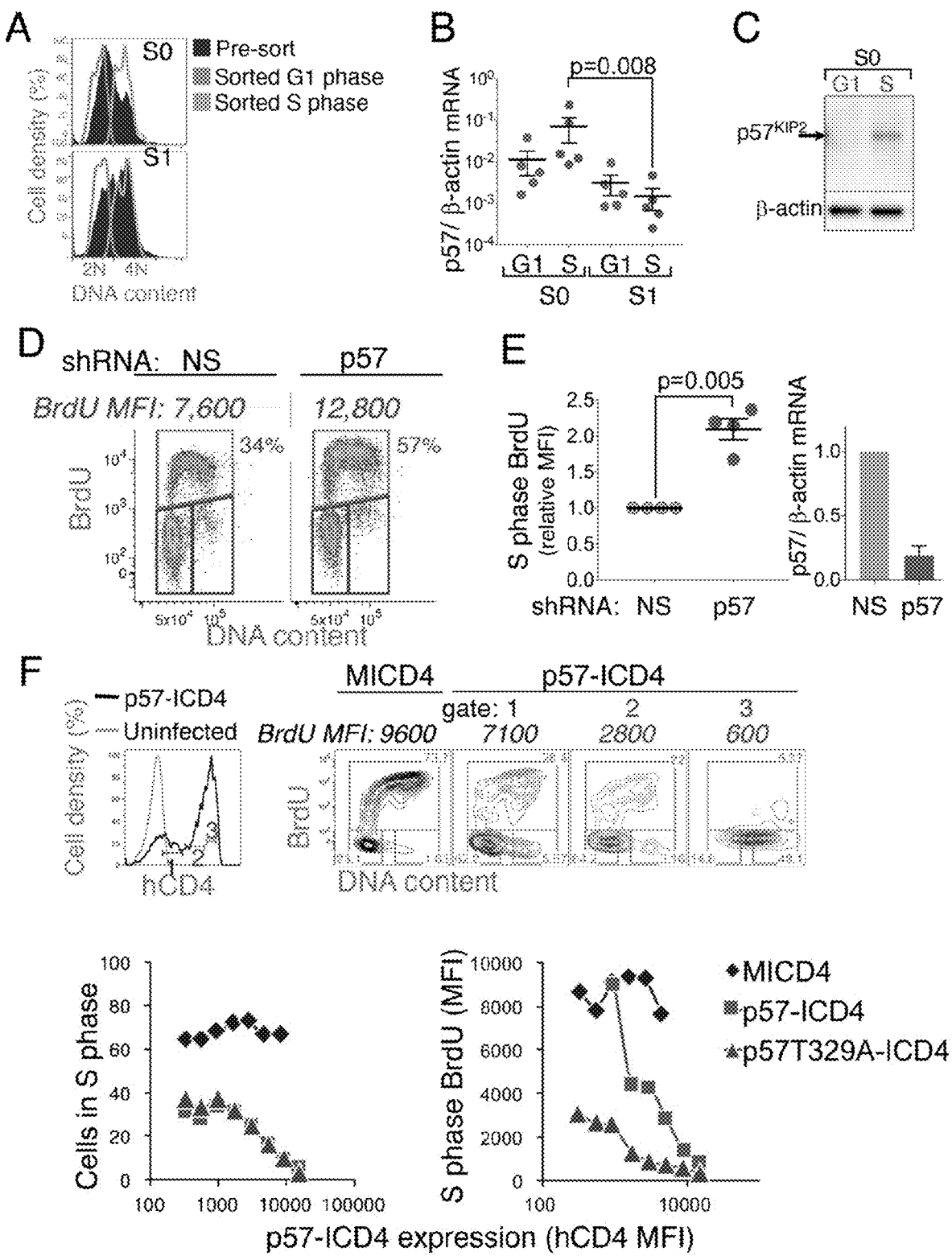

where
f=cells that exited S phase in interval I, measured as % (EdU$^+$BrdU$^-$) cells
I=interval between the EdU and BrdU pulses
Tc=cell cycle length
This relationship gives the length of the cycle as Tc=I/f
The length of S phase, Ts, can then be calculated from fraction s, of all cycling cells that take up the BrdU label (% BrdU$^+$), as $$Ts = s \times Tc$$

where
s=% BrdU$^+$ cells
Ts=length of S phase
In preliminary experiments, we used longer BrdU pulses. These showed that nearly all cells labeled with BrdU, suggesting that essentially all cells are cycling. Therefore, we made no corrections for the fraction of cycling cells.

(1C) Representative experiment as described in (B). Pregnant female mice were pulsed with EdU, followed by a BrdU pulse after an interval of 2 hours. Upper two panels show fetal liver cells from mice that were pulsed only with EdU, or only with BrdU, but processed for labeling for both deoxynucleosides in the same way as the double-labeled mice. Lower panels show EdU and BrdU labeling in fetal liver subsets that were explanted after the second pulse, sorted by flow cytometry, and then each processed for EdU and BrdU incorporation. In this specific experiment, a third of all S1 and S2 cells exited S phase in a 2 hour interval, giving a cell cycle length of 2/0.33=6 hours; only 14% of S0 exited S phase in the same time interval, giving a cell cycle length of 2/0.14=14.3 hours. Since 64% of S1 and 44% of S0 cells are BrdU+, their S phase lengths are 0.64×6=3.84 hours and 0.44×14.3=6.3 hours, respectively.

(1D) Summary of 5 independent experiments as described above. The linear relationship between/and the cells that exited S phase, f, allows calculation of a mean cycle and length. Empty symbols=S1, filled symbols=S0. R squared=0.95 for S1, 0.85 for S0. Results in table are mean±SE. Pulses were reversed (BrdU first, EdU second) in one experiment, without effect on results (included here). Of note, lines do not intercept the y axis at 0 since it takes approximately 20 minutes for peak absorption of each deoxynucleoside (fetal livers are explanted 20 minutes following the second injection).

(1E) Durations of cell cycle and cell cycle phases. The length of each cell cycle phase was calculated by multiplying the fraction of cells in each cell cycle phase following the second pulse, by the total cell cycle length (measured as in (D)).

FIGS. 2A-2F. p5$^{KIP2}$ regulates intra-S phase DNA synthesis rate (2A) DNA content histograms of freshly explanted and sorted fetal liver cells enriched for either G1 or S phase, from either the S0 or S1 subsets. DNA content histograms of the sorted subsets are overlaid on the DNA content histograms of the parental S0 or S1 populations. DNA content was visualized with the DNA dye Hoechst 33342. Representative of 5 independent sorts.

(2B) p57$^{KIP2}$ mRNA expression is highest in S phase of S0 cells. qRT-PCR was performed in samples sorted as in (A). Data are mean±sem for five independent sorting experiments. Statistical significance was assessed with the Mann Whitney test.

(2C) Western blotting on fetal liver samples sorted as in (A). Representative of two experiments, each with 30 fetal livers.

(2D) Intra-S phase DNA synthesis rate following retroviral transduction of S0 cells with shRNA targeting p57$^{KIP2}$ or with a non-silencing control shRNA (NS). Cells were pulsed with BrdU for 30' twenty hours post transduction.

(2E) Summary of 4 independent p57$^{KIP2}$ knock-down experiments as in (D). Intra-S phase DNA synthesis is expressed relative to controls transduced with non-silencing shRNA. Samples were pulsed with BrdU for 30 minutes, 20 to 60 hours following transduction. Statistical significance assessed with a paired t test.

(2F) p57$^{KIP2}$ exerts dose-dependent inhibition of DNA synthesis within S phase cells. S0 cells were transduced with p57$^{KIP2}$-hCD4 (ICD4) or with 'empty' vector (MICD4). Eighteen hours post transduction, cells were pulsed with BrdU for 30'. Transduced cells were divided into gates 1, 2, & 3 (top left panel), expressing increasing levels of hCD4. Corresponding cell cycle analyses for each gate are shown (top right panels), including BrdU MFI for the S phase gates in italics. See also FIG. S2. Lower panels: similar analysis relating MICD4, p57-ICD4 or p57T329A-ICD4 expression (hCD4-MFI) with either the number of cells in S phase (lower left panel) or BrdU MFI (lower right panel). Representative of 6 independent experiments.

FIGS. 3A-3G. Anemia and abnormal erythropoiesis in p57$^{KIP2}$-deficient embryos (3A) p57$^{KIP2}$+/−$^m$ and wild-type littermate embryos, at E13.5. The p57$^{KIP2}$+/−$^m$ embryo is pale and has a smaller fetal liver.

(3B) p57$^{KIP2}$-deficient embryos are anemic, as seen from their significantly reduced hematocrit (n=64 embryos, E13.5).

(3C) Fewer fetal liver cells in p57$^{KIP2}$-deficient p57$^{KIP2}$ embryos compared with wild-type littermates (n=121 embryos).

(3D) Abnormal erythroid differentiation in p57$^{KIP2}$-deficient embryos. A representative CD71/Ter119 plot showing fewer S3 erythroblasts in the p57$^{KIP2}$–/– embryo compared with wild-type littermate.

(3E) Increased frequency of S0 cells in p57$^{KIP2}$ deficient fetal livers, measured as in (3D), from 7.9±0.46% (mean±SE, wild-type embryos, n=36) to 10.6±1% (p57$^{KIP2}$–/–, n=14) and 10.0±0.38 (p57$^{KIP2}$–/–$^m$, n=25). The absolute number of S0 cells is unchanged since the total number of fetal liver cells is reduced proportionally, to 67% of wild-type, for both p57$^{KIP2}$–/–$^m$ and p57$^{KIP2}$–/– embryos (see (C)).

(3F) Reduced ratio of S3 to S0 erythroblast number, measured as in (D), for a total of 74 embryos.

(3G) Inverse correlation between apoptosis in the S0 or S1 subsets, and S3 frequency, in the fetal livers of p57$^{KIP2}$-deficient embryos. No significant correlation seen in the fetal livers of wild-type littermates. Fetal livers were freshly explanted and immediately stained for Annexin V binding. n=75 embryos.

FIGS. 4A-4F. Prematurely short S phase and replication-associated DNA damage in p57$^{KIP2}$-deficient fetal liver (4A) Premature increase in intra-S phase DNA synthesis rate, measured as BrdU MFI, in p57$^{KIP2}$-deficient embryos. Representative cell cycle analysis of p57$^{KIP2}$+/–$^m$ and wild-type littermate embryos. Embryos were pulsed in vivo with BrdU for 30' before fetal livers were explanted.

(4B) Premature increase in intra-S phase DNA synthesis rate in p57$^{KIP2}$-deficient embryos. Data summary, analyzed as in (A); n=29 (+/+), 12 (–/–), 18 (+/–$^m$). For each embryo, S phase BrdU MFI in S0 is expressed as a percentage of S phase BrdU MFI in S1 of the same fetal liver.

(4C) Increased γ-H2AX in S0 cells of p57$^{KIP2}$-deficient embryos. Representative examples of freshly explanted fetal livers of p57$^{KIP2}$-deficient embryos and wild-type littermates, labeled with an antibody against γ-H2AX. DNA content was measured using 7AAD. See also FIG. 9.

(4D) Increased γ-H2AX in S0 cells of p57$^{KIP2}$-deficient embryos. Summary of data obtained as in (C) for a total of n=79 embryos. γ-H2AX measured in arbitrary fluorescence units.

(4E) Distribution of γ-H2AX labeling, DNA content and BrdU incorporation in G1, S, or G2/M phases of the cell cycle and in γ-H2AX-positive cells, all in the S0 subset of a single p57$^{KIP2}$–/– fetal liver. Embryos were pulsed in vivo with BrdU for 30', fetal livers were harvested, fixed and labeled for BrdU incorporation, DNA, and γ-H2AX. S0 cells were subdivided digitally into cell cycle phase gates based on their DNA content and BrdU incorporation. Cells positive for γ-H2AX were gated based only on γ-H2AX signal regardless of cell cycle phase.

(4F) p57$^{KIP2}$ deficient γ-H2AX-positive S0 cells are slowed or arrested in S phase. Data summary for 17 p57$^{KIP2}$–/+$^m$ fetal livers, analyzed as in (E). Each datapoint is BrdU MFI (bottom) or median DNA content (top) for all cells in a specific category (G1, S, G2/M or γH2AX-positive) in a single fetal liver. BrdU MFI and median DNA content were normalized to their respective values in G1 cells of the S0 subset in each fetal liver.

FIGS. 5A-5J. p57$^{KIP2}$ is essential to CFUe self-renewal in vitro (5A) p57$^{KIP2}$ mRNA levels during CFUe self-renewal in vitro, and following the switch to differentiation. Wild-type S0 cells were cultured for 5 days in self-renewal medium ('Dex+Epo'). Cells were washed and then either placed in differentiation medium ('Epo'), or back in self-renewal medium ('Epo+Dex'). Dex withdrawal leads to rapid down-regulation of p57$^{KIP2}$ and to concurrent rapid induction of erythroid genes such as α or β-globin. mRNA measured by qRT-PCR, normalized to β-actin and expressed relative to t=0.

(5B) Western blot and protein band quantification during CFUe self-renewal in vitro, and following the switch to differentiation. Experiment as in (A); on day=0, CFUe were either replaced in self renewal medium ('Epo+Dex') or in differentiation medium ('Epo'). The p57$^{KIP2}$ band was identified using control cells transduced with retroviral vector expressing p57$^{KIP2}$ as in (E) below (not shown). The uppermost band on the p57$^{KIP2}$ blot is an unrelated cross-reacting band seen in 'Epo+Dex' cultures (see (E) below). Legend as in (A), except green diamonds=α-globin.

(5C) Cell cycle status of CFUe during self-renewal in vitro ('Epo+Dex'), and 20 to 60 hours following Dex withdrawal ('Epo'). BrdU MFI in 'Epo' is expressed relative to its value in matched control cells undergoing Dex-dependent self-renewal. Upper panel: representative example; lower panel, summary of 7 matched cultures from 3 independent experiments. Statistical significance: paired t test.

(5D) p57$^{KIP2}$-deficient S0 CFUe cells fail to self-renew in vitro. S0 cells derived from individual wild-type or littermate p57$^{KIP2}$-deficient fetal livers were cultured in medium containing Epo+Dex. Cell numbers are relative to t=0, mean±SE of 4 (for +/–$^m$) or 5 (for –/–) embryos. See also FIG. 10A.

(5E) Western blot of p57$^{KIP2}$ protein on day 9 of Dex-dependent CFUe self-renewal in vitro. Control 3T3 cells transduced with either empty vector or vectors expressing each of two p57$^{KIP2}$ isoforms are also shown. Fetal liver cells express only the shorter, 335 amino-acid isoform of p57$^{KIP2}$. Low levels of the p57$^{KIP2}$ protein are also detectable in p57$^{KIP2}$+/–$^m$ cells following 9 days of culture in Epo+Dex (see also FIG. 10 B, C). Note that the top band is an unrelated cross reacting band.

(5F) Increased intra-S phase DNA synthesis rate in p57$^{KIP2}$-deficient CFUe undergoing Dex-dependent self-renewal in vitro for 6 days. BrdU MFI in the S phase gate is expressed relative to the wild-type littermate value. Representative of 3 independent experiments.

(5G) Increased number of γH2AX-positive cells in p57$^{KIP2}$ CFUe undergoing Dex-dependent self-renewal, relative to wild-type littermate culture. Representative of 3 independent experiments.

(5H) p57$^{KIP2}$ rescued p57$^{KIP2}$ deficient CFUe self-renewal. p57$^{KIP2}$ deficient S0 cells were transduced with low titre virus (viral supernatant at the indicated dilutions) encoding p57$^{KIP2}$, or with empty vector. Cells transduced with p57$^{KIP2}$ showed significant improvement in self-renewal. Wild-type S0 cells transduced in parallel showed a reduction in self-renewal rate.

(5I) The CDK inhibitor drug, roscovitine, rescued self-renewal of p57$^{KIP2}$ deficient CFUe. p57$^{KIP2}$–/– S0 cells and wild type S0 cells from littermate embryos were harvested and cultured in self renewal medium containing Epo+Dex, in the presence or absence of roscovitine. See also FIG. 12B. The same data is shown twice, with γ-axis as logarithmic or linear scale. Amplification of wild-type cells is also enhanced in the presence of roscovitine.

(5J) Effect of roscovitine on amplification of wild-type CFU-e in Dex cultures. Roscovitine was added at the indicated concentrations.

FIGS. 6A-6E. Global increase in replication fork speed at the transition from S0 to S1, regulated by p57$^{KIP2}$.

(6A) Experimental design. Fetal livers were individually explanted and allowed to recover for 4 h at 37° C. Following genotyping, all embryos of the same genotype (either +/+ or +/−$^m$) were pooled and pulsed with IdU for 10', followed by CldU. Cells were then placed at 4° C., sorted into S0 and S1 subsets by flow cytometry, and processed for DNA combing.

(6B) Portion of a DNA fiber illustrating the identification and measurement of replication structures. For clarity, the same fiber is shown twice, with (bottom) or without (top) the blue fluorescence channel. IdU tracks label green, and are used to measure fork speed. CldU tracks label red or yellow, since, in addition to CldU (red) they contain DNA incorporating residual IdU (green). The red/yellow tracks are used to obtain fork directionality. Note that fiber sections where there is equal staining for red, blue and green (which may occur during the second pulse) the fiber appears white (the sum total of red, green and blue in the RGB color format); this does not reflect saturation of signal. See also FIGS. 15A-15C for an example of a full microscope field.

The blue fluorescence allows assessment of the DNA fiber continuity between replication bubbles or forks. This therefore allows localization of origins (marked 'o'), as either equidistant from two forks proceeding in opposite directions, or in the center of a green (IdU) track bordered by two red (CldU) tracks. The former is an origin that fired prior to the IdU pulse, whereas the latter is an origin that fired during the IdU pulse. Identification of origins allows the measurement of inter-origin distances as shown. Fork speed was measured as the length of green (IdU) tracks, in kb, for forks that moved throughout the IdU pulse (immediately adjacent blue, green and red tracks), and divided by the duration of the pulse (10').

(6C) Scatter plots showing inter-origin distances (top) and fork speeds (bottom) for a single experiment in which littermates p57$^{KIP2}$+/−$^m$ and wild-type embryos were analyzed. See FIGS. 13A-13B for additional analysis including fiber length distributions. p values are for a two-tailed t-test of unequal variance between the indicated samples. Inter-origin distance was not significantly different between any of the samples.

(6D) Examples of fork trajectories during the 10' IdU pulse, from the dataset in 'C'. The yellow dashed line indicates the transition from IdU to CldU. Only the IdU track was used for measurement of fork speed.

(6E) Violin plots for the data shown in 'C'. There is a substantial shift between the distributions of wild type S0 and S1, and between wild-type and p57$^{KIP2}$+/− in S0 cells.

FIGS. 7A-7D. The transition from self-renewal to differentiation at S0/S1 is associated with a transient increase in intra-S phase DNA synthesis rate (7A) Flow-cytometric profile of the fetal liver at embryonic day 13.5 (E13.5), divided into subsets S0 to S5 based on cell surface expression of CD71 and Ter119. Cells expressing non-erythroid markers were depleted prior to analysis as described (23).

(7B) Schematic illustrating the measurement of intra-S phase DNA synthesis rate using BrdU incorporation rate. All cells are subjected to the same 30' BrdU pulse. Cells in S phase during the pulse incorporate BrdU into nascent DNA, becoming BrdU-positive. Cells in which S phase is shorter replicate their genome faster, so that the total length of BrdU-labeled nascent DNA is longer than in cells with a slower S phase. The amount of BrdU incorporated into S phase cell populations may be measured as the median fluorescence intensity of the BrdU signal (BrdU MFI) in BrdU+ cells and is proportional to the median intra-S phase DNA synthesis rate.

(7C, 7D) Cell cycle status of fetal liver subsets S0 to S5. (7C) shows flow cytometric profiles, (7D) shows quantitation of the same data. A pregnant female mouse was pulsed in vivo with BrdU for 30' before harvesting fetal livers. Shown is an example of a single fetal liver, from the same embryo illustrated in (7A). Cells were sorted digitally into subsets S1 to S5. The number of S phase cells and BrdU MFI were measured for each subset. The data are similar to data from pooled fetal livers published previously.

Figure 8:
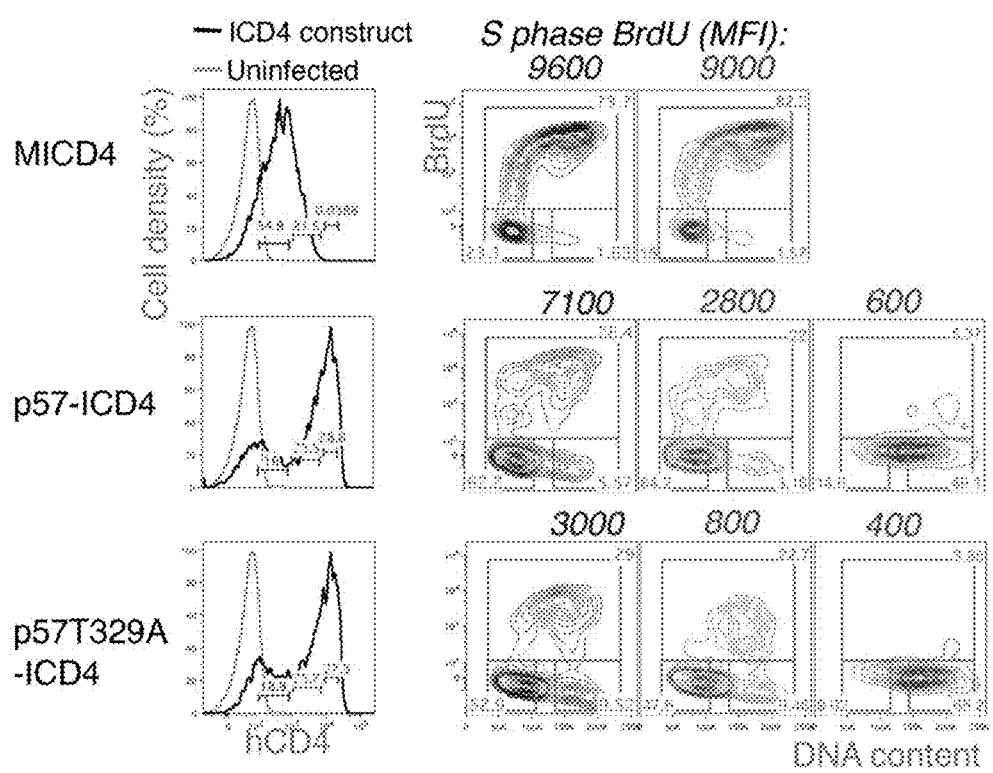

FIG. 8. p57$^{KIP2}$ exerts dose-dependent inhibition of DNA synthesis within S phase cells.

See also FIG. 2F.

Experiment as described in FIG. 2F. Shown are 3 hCD4 gates for each of the transduced constructs, with corresponding cell cycle analysis. BrdU MFI is noted in italics above each plot.

Figure 9A:
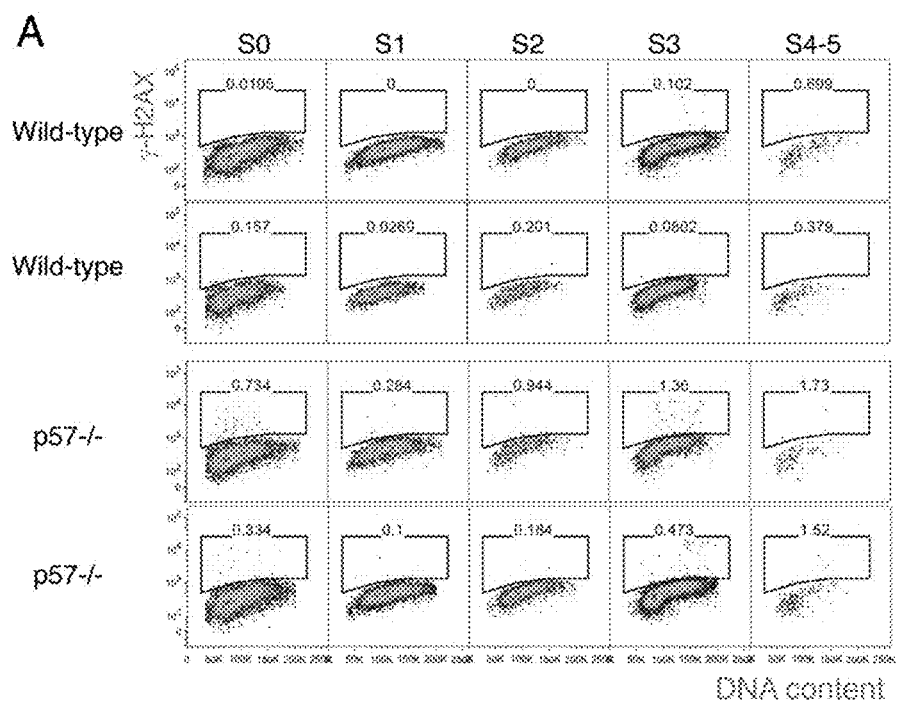
Figure 9B:
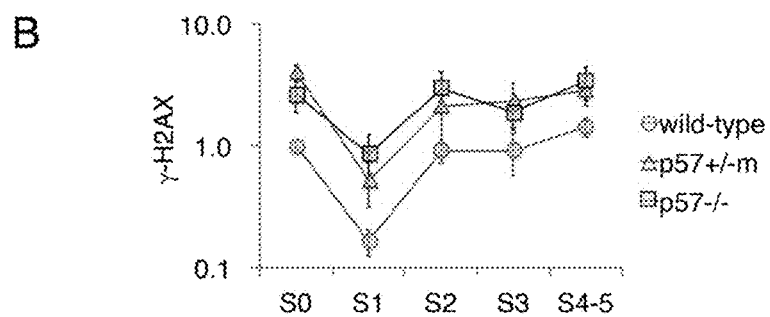

FIGS. 9A-9B. Increased γH2AX in p57$^{KIP2}$-deficient fetal liver.

See also FIG. 4C-F.

(9A) Freshly explanted fetal livers of p57$^{KIP2}$-deficient embryos and wild-type littermates were labeled with an antibody against γ-H2AX. DNA content was measured using 7AAD. Representative examples are shown for littermate embryos for each of subsets S0 to S5.

(9B) Data summary for 71 embryos, experiment as described in (A). γ-H2AX levels are expressed relative to the mean γ-H2AX signal in wild-type S0 cells of each litter. Differences between p57$^{KIP2}$ deficient embryos and wild-type littermates are significant (paired t test, p=0.005 and 0.025 for p57$^{KIP2}$−/− and p57$^{KIP2}$−/+$^m$, respectively).

Figures 10A, 10B, 10C:
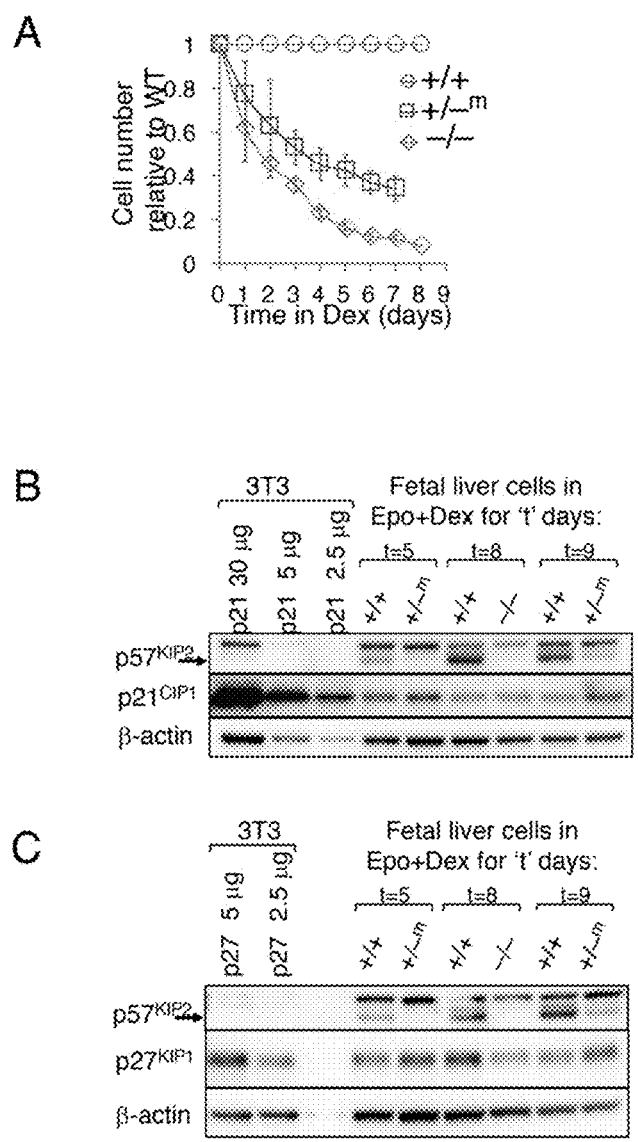

FIGS. 10A-C. Analysis of p57$^{KIP2}$-deficient CFUe undergoing self-renewal in vitro.

(10A) p57$^{KIP2}$-deficient S0 cells fail to self-renew in vitro. Data as in FIG. 5D, but cell number is normalized to the respective wild-type cell number in each experiment.

(10B), (10C) Western blots showing no consistent compensatory upregulation of either p21$^{CIP1}$ (10B) or p27$^{KIP1}$ (10C) during 9 days of Dex-dependent S0 CFUe expansion in vitro. Control 3T3 cells were transduced with empty vector, or with vectors encoding either p21$^{CIP1}$ or p27$^{KIP1}$. Low levels of the p57$^{KIP2}$ protein in p57$^{KIP2}$+/−$^m$ cells accumulate with increasing time of culture in self renewal medium (Epo+Dex).

Figure 11:
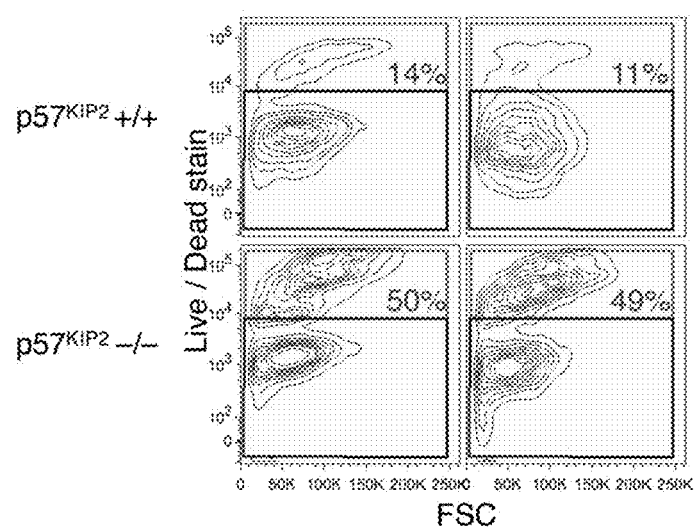

FIG. 11. Increased cell death in p57$^{KIP2}$ S0 CFUe during self-renewal in vitro Cell death (upper gate, red) was measured by staining with the 'Live/Dead' reagent (Invitrogen), in cells undergoing Dex-dependent self-renewal in vitro. Two representative cultures of p57$^{KIP2}$−/− fetal livers are compared with two cultures of fetal livers from wild-type littermates, on day 4 of culture.

FIGS. 12A-12B. CFUe self-renewal requires the CDK binding and inhibition functions of p57$^{KIP2}$ (12A) Upper panel: S0 cells were transduced with wild-type p57$^{KIP2}$ or with the indicated p57$^{KIP2}$ mutants. The hCD4 reporter fluorescence identifies transduced cells.

Lower panels: Cell cycle status, including intra-S phase DNA synthesis rate (BrdU MFI in the red gate, in red italics), for S0 cells that were transduced with the indicated constructs. Cell cycle analysis was done 15 hours post transduction. MICD4='empty' vector expressing only IRES-hCD4.

Figures 5A, 5B, 5C, 5D, 5E, 5F, 5G, 5H:
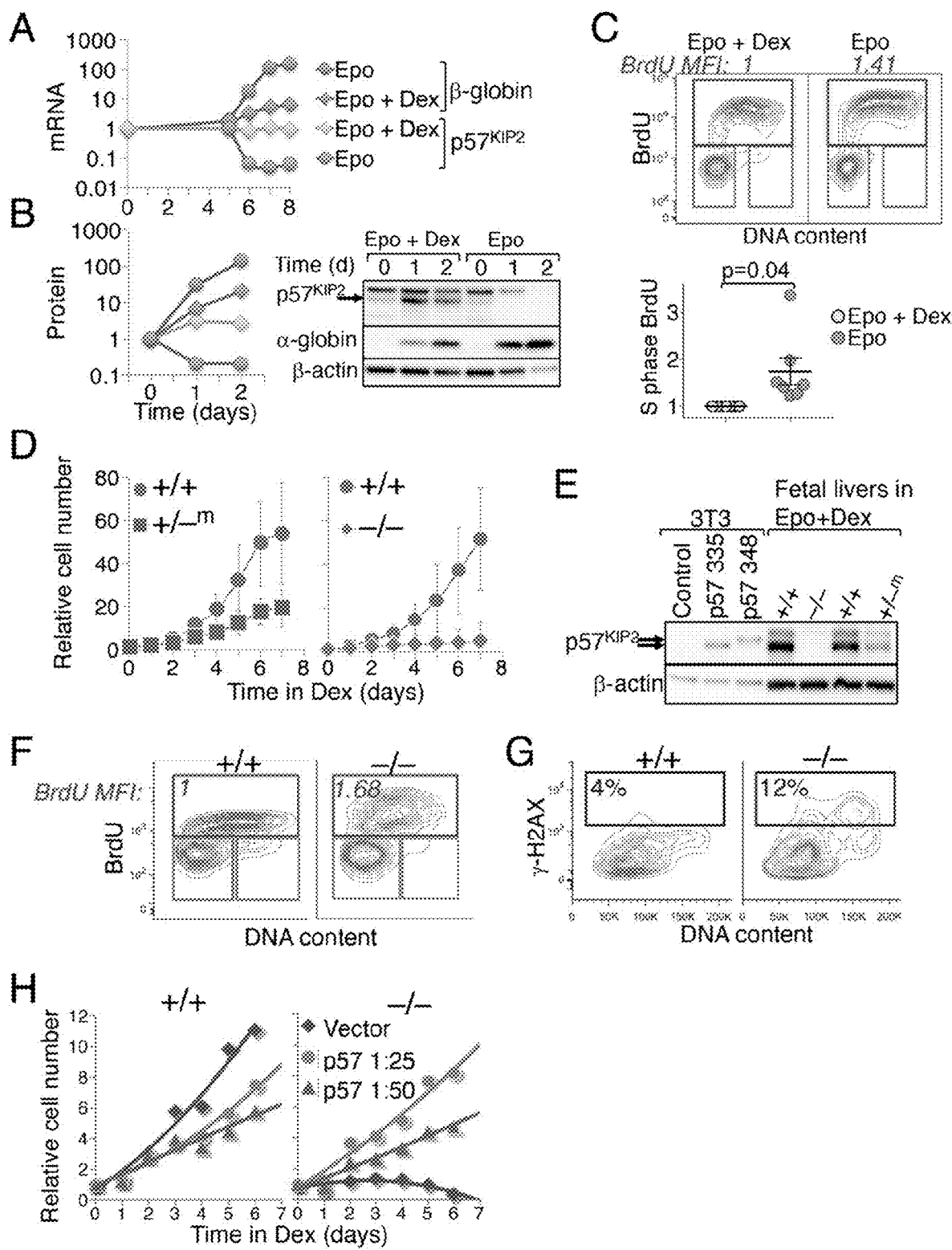
Figure 5I:
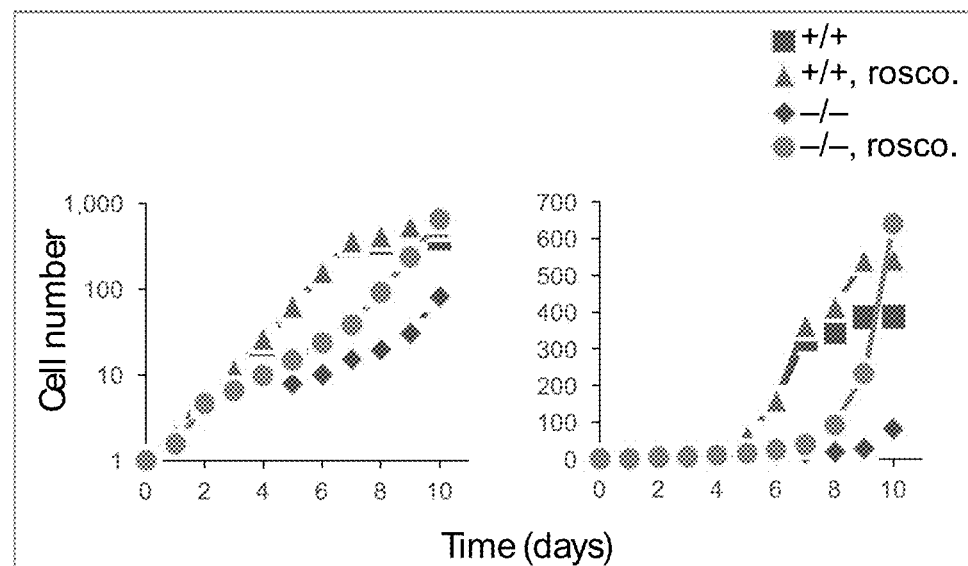

(12B) Analysis of CFUe potential in Dex-dependent self-renewal cultures of p57$^{KIP2}$−/− cells treated with roscovitine (See FIG. 5I). On day 11 of culture, cells amplified in the presence or absence of roscovitine were plated at 10$^5$ cells per dish in Epo-containing semi-solid medium. The number of CFUe colonies formed per dish was scored 72 hours following plating. This analysis shows that the CFUe colony forming potential of roscovitine treated cells is similar to that of untreated cells (data are means of two duplicates per conditions). Therefore, the increased cell number in roscovitine-treated p57$^{KIP2}$–/– cultures (See FIG. 5I) reflects a genuine increase in CFUe self-renewal.

Figure 13A:
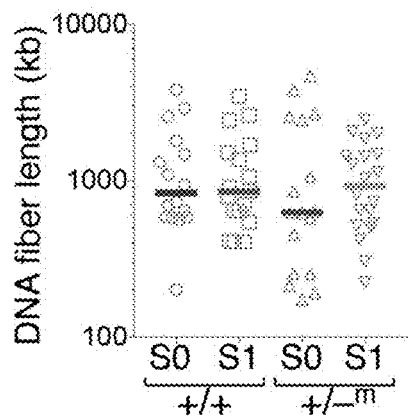
Figure 13B:
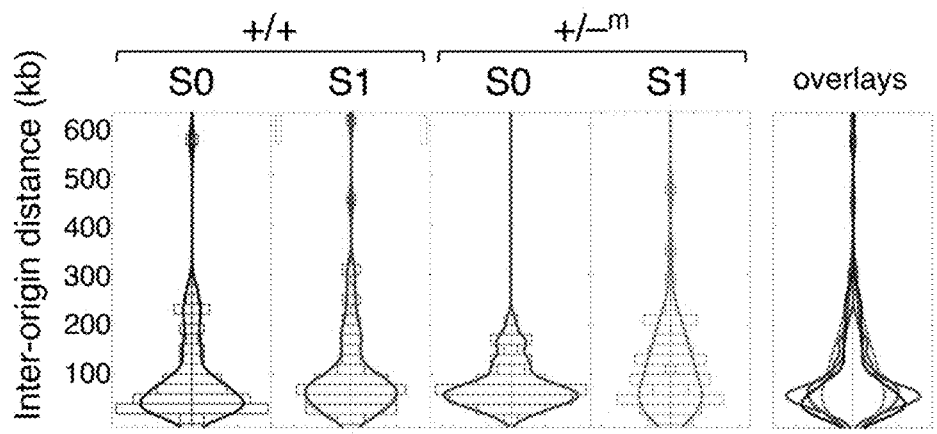

FIGS. 13A-13B. DNA combing analysis of freshly explanted fetal livers from wild-type and p57$^{KIP2}$+/–$^m$ embryos-associated with experiment in FIG. 6.

Figures 6A, 6B, 6C, 6D, 6E:
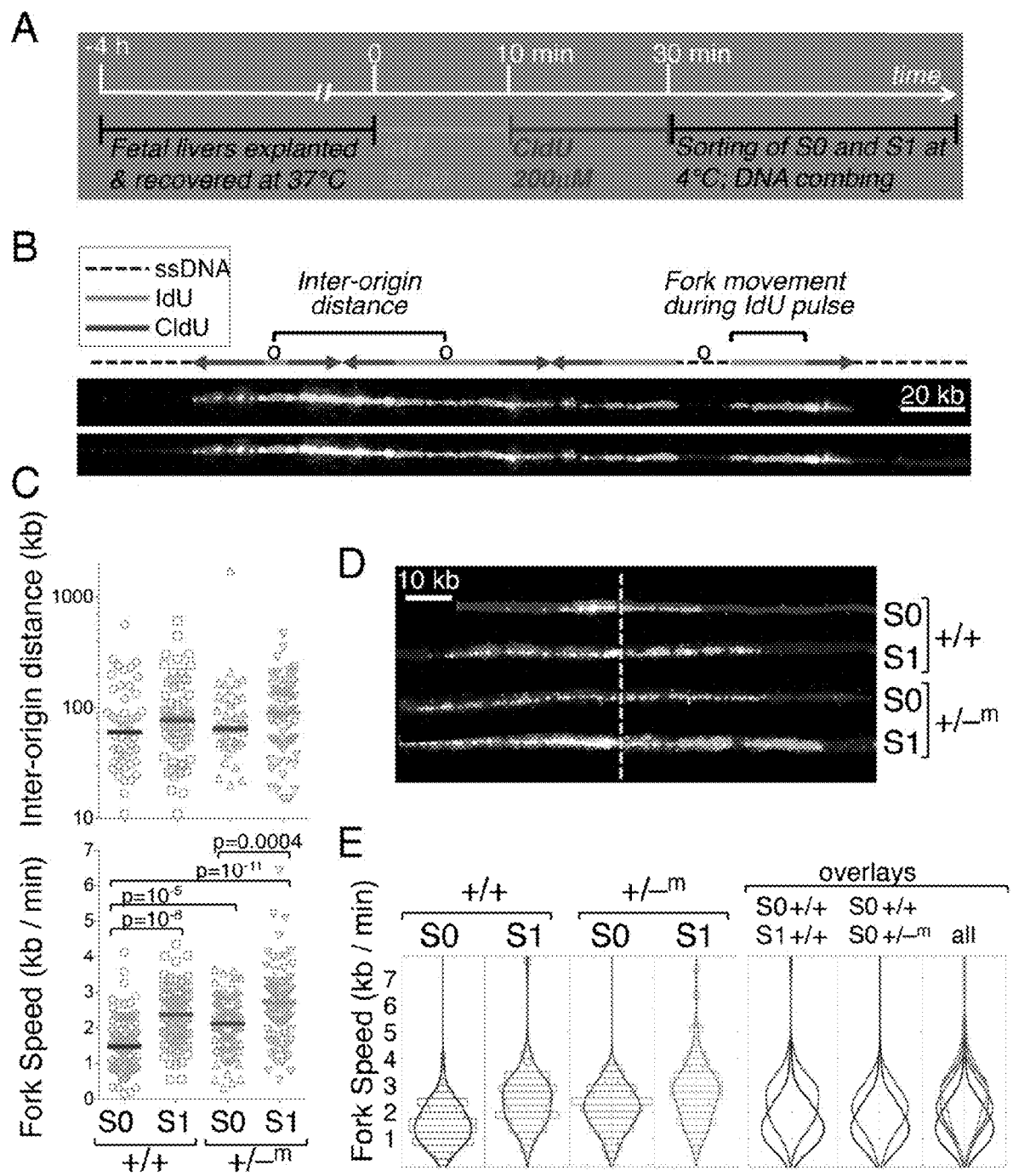

(13A) Scatter plots for inter-origin distance distributions, same data as in FIG. 6C.

(13B) Violin plots for the DNA fiber lengths used in the experiment shown in this FIG. and in FIG. 6. The table shows total number, mean, standard deviation and sum of all analyzed DNA fibers for each cell type.

Figures 14A, 14B, 14C:
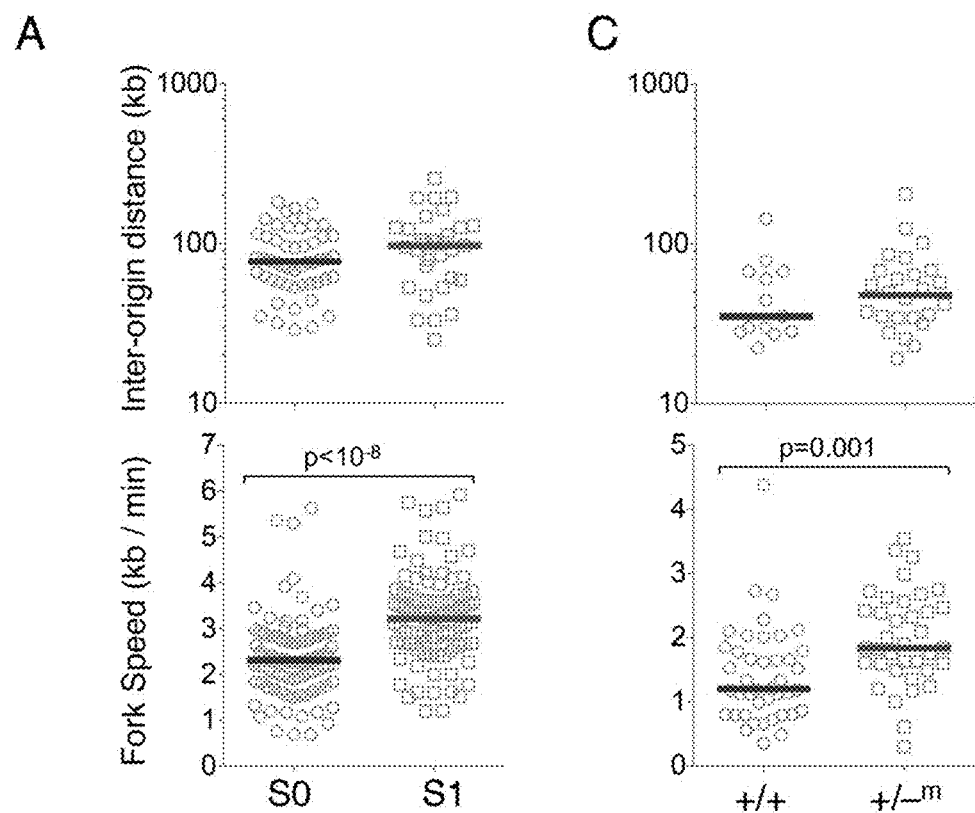

FIGS. 14A-14C. DNA combing experiments.

(14A) DNA combing analysis of freshly explanted wild-type fetal liver from the Balb/C mouse strain. This is an independent experiment from the one presented in FIG. 6 and FIG. 13. Experimental design as described in FIG. 6A. A total of 90 (S1) and 92 (S0) forks that moved throughout the IdU pulse are compared.

(14B) DNA fiber statistics for the experiment illustrated in (14A).

(14C) A DNA combing experiment of Dex-dependent cultures in which S0-derived CFUe undergo self-renewal. Two cultures, from wild-type and p57$^{KIP2}$+/–$^m$ littermates, were analyzed on day 5 of the culture. A total of 8 Mb of DNA were examined, mean fiber length=384 kb.

Figure 15A:
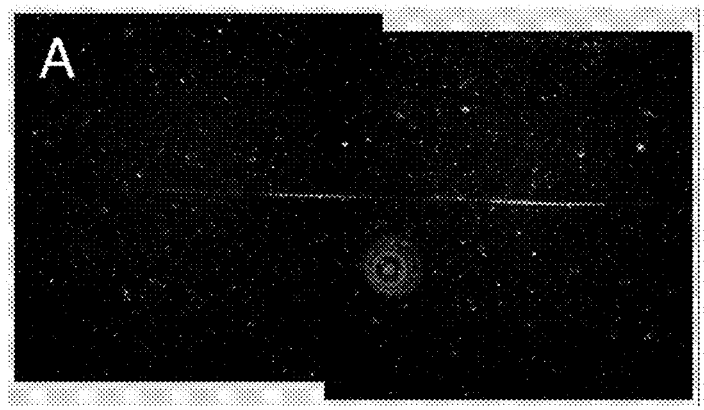
Figure 15B:
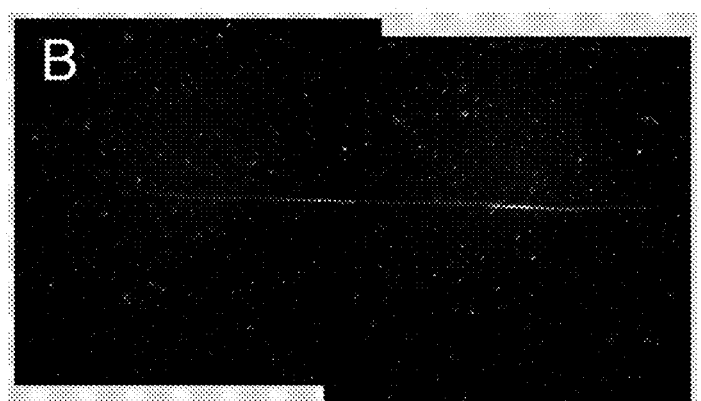
Figure 15C:
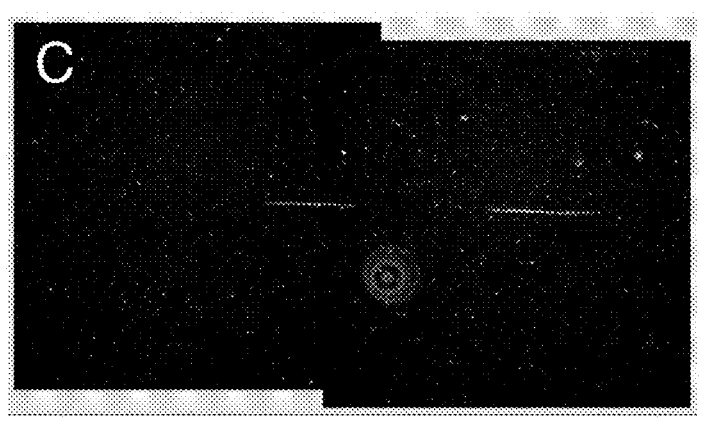

FIGS. 15A-15C. DNA combing: example of fluorescence image file used for scoring data.

A DNA fiber spanning two partly overlapping microscope fields of view. Total fiber length (entire blue track) is 376 kb. Three exposures were taken for each field, separately capturing green, red and blue fluorescence. The three fluorescence images for each field were digitally merged into a single file. The two merged files, each corresponding to a field of view, were then aligned to reproduce the full length of the fiber in a composite image shown above. In FIGS. 15A, 15B and 15C, are shown either all colors, or just two of the three colors in the image. Average image files used for the DNA combing data were composites of up to 30 microscope fields.

FIGS. 16A-16D. CDK inhibition enhances Dex-dependent growth of erythroid progenitors Adult bone marrow mononuclear cells (StemCell Technologies) (A), mouse fetal liver (B) and mouse adult bone marrow (C-D), were cultured in the presence of Dex, Epo, SCF and IGF-1. Dex slows down and delays the transition from self-renewal to differentiation of early CFU-e progenitors, leading to their numerical amplification.

(16A) Addition of roscovitine allowed human bone-marrow cultures to reach a peak, 9-fold amplification on day 16, compared with a peak of 5-fold amplification on day 14 in control cultures (p=0.027 when comparing the roscovitine with control cultures for the entire 18 day culture period; p=0.00001 when comparing the cultures between days 8 and 18 only; two-tailed paired t test, unequal variance). Results pooled from two independent experiments, each containing 2 biological replicates for control cultures and two roscovitine-treated replicates.

(16B) Similar increased amplification of erythroid cell number in response to roscovitine in cultures of mouse fetal liver. Representative of 3 independent experiments.

(16C), (16D) Two independent experiments showing improved growth of mouse bone marrow erythroid progenitors in response to roscovitine or the selective CDK2 inhibitor SC-221409; the selective CDK4 and CDK6 inhibitor, PD033299, resulted in growth inhibition. All CDK inhibitor drugs were used at a concentration corresponding to five time their respective IC$_{50}$.

Figures 17A, 17B:
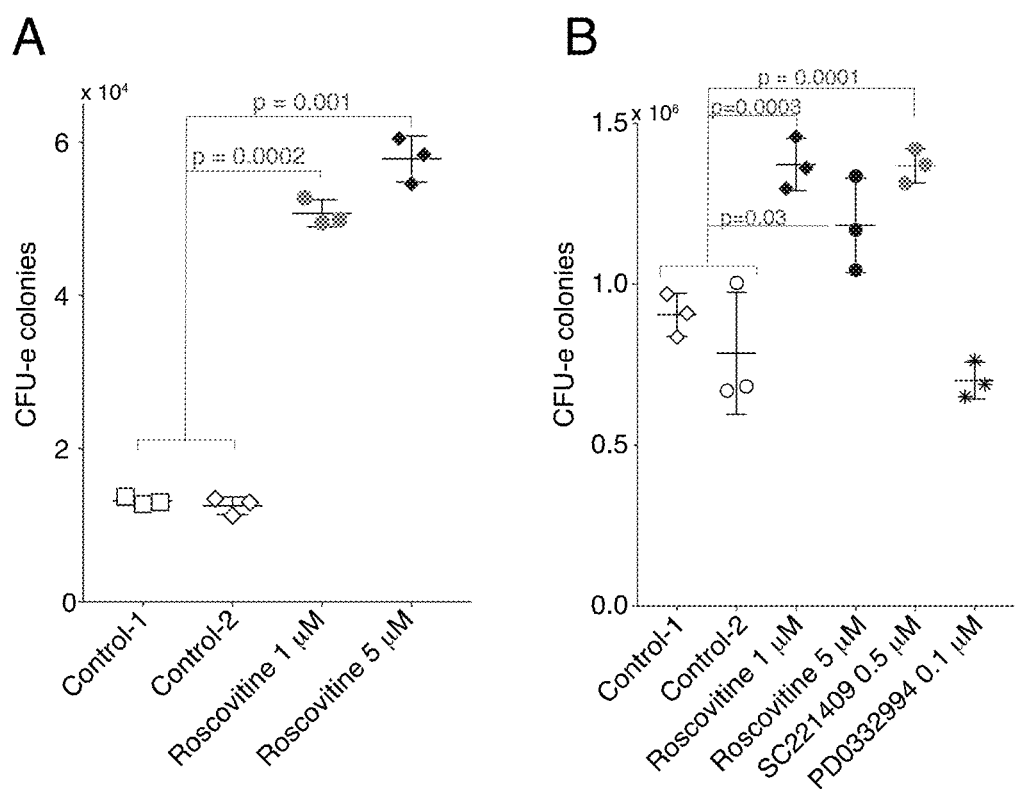

FIGS. 17A-17B. CDK inhibition enhances the self-renewal of erythroid progenitors with CFU-e colony forming potential (17A) Human bone-marrow erythroid progenitors were amplified in cultures as in FIG. 1A. On day 11 of culture, cells were plated in semi-solid methylcellulose medium under differentiation conditions (in the presence of Epo and in the absence of Dex or SCF). CFU-e colonies were scored at 72 hours using diaminobenzidine staining to identify hemoglobinized cells. The absolute number of CFU-e progenitors obtained from the same initial starting number in each culture is shown. All statistically significant differences are noted (two-tailed t test, unequal variance).

(17B) Mouse bone marrow erythroid progenitors, treated as described in A, but plated on day 5 of the culture in semi-solid medium, CFU-e colonies scored 72 hours later. In addition to roscovitine, the effects of SC-221409 and PD033299 are also shown.

Figure 18A:
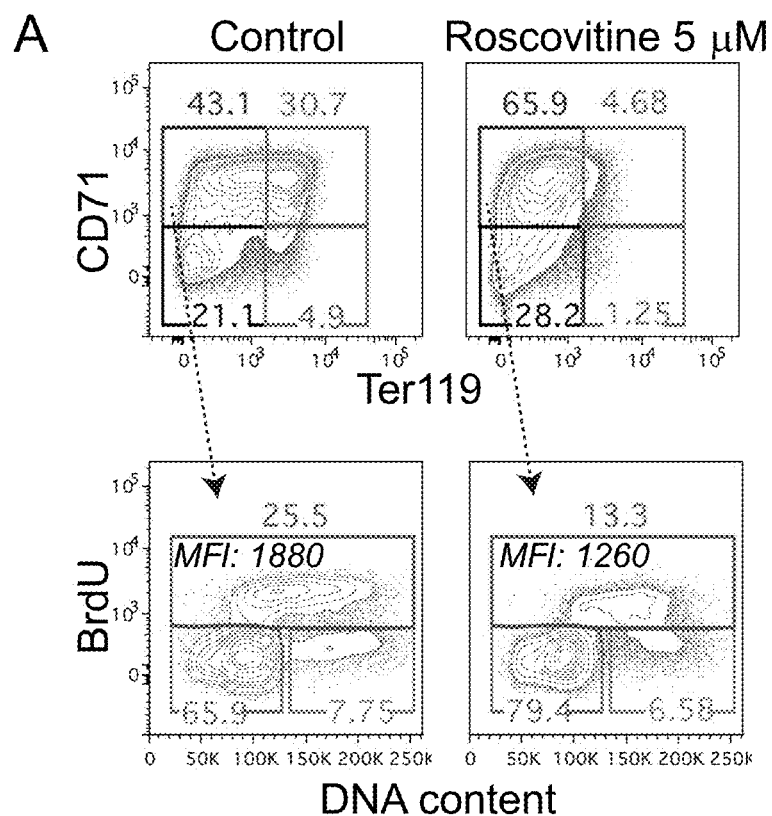
Figure 18B:
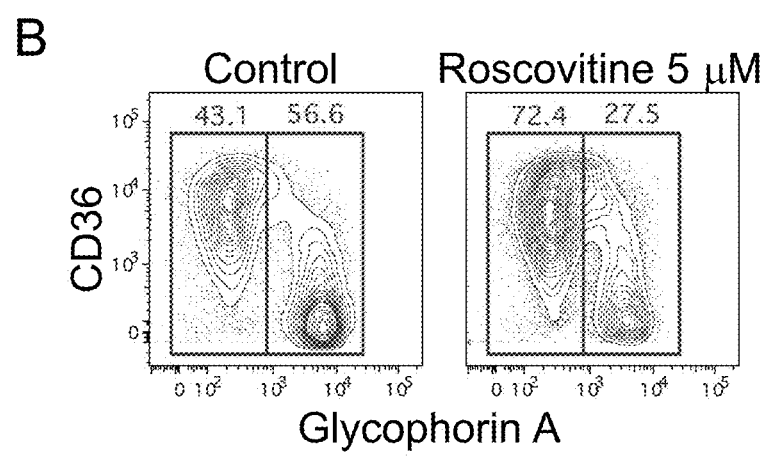

FIGS. 18A-18B. Flow-cytometric analysis shows that CDK2 inhibitors delay erythroid differentiation (18A) Flow cytometric analysis of mouse bone marrow self-renewing cultures, on day 6 of culture. Top panels: The relative absence of terminally-differentiating Ter119+ erythroblasts in roscovitine-treated cultures compared with control, suggest that roscovitine delays differentiation. The overall viability of cells in roscovitine-treated cultures was increased (not shown). Bottom panels: corresponding cell cycle analysis of cells in each culture. Cells were pulsed with BrdU at 33 µM for 25 min before analysis. Roscovitine treatment resulted in fewer S phase cells, and in a slower S phase, as indicated by the reduced bromodeoxyuridine (BrdU) incorporation, measured as BrdU median fluorescence intensity (MFI) in the S phase gate (indicated).

(18B) Flow cytometric analysis of human bone marrow self-renewing cultures, on day 10 of culture. Roscovitine treatment inhibits terminal differentiation and promotes self-renewal, as indicated by the lower number of cells that express the glycophorin A cell surface marker, an indicator of terminally differentiating erythroblasts.

DETAILED DESCRIPTION

Recently, an S phase-dependent cell fate decision was identified that controls the transition from self-renewal to differentiation in the murine erythroid lineage (23). Erythroid progenitors at the colony-forming-unit-erythroid (CFUe) stage (24) undergo a number of self-renewal cell divisions before switching into a phase of active erythroid gene transcription, known as erythroid terminal differentiation (ETD), during which they mature into red cells while undergoing 3 to 5 additional cell divisions. The switch from self-renewal to ETD is tightly regulated, since it determines the number of CFUe progenitors and erythroid output (24, 25). Many of the transcription factors that drive the ETD, including GATA-1, Tal-1 and Klf1, are well characterized (26, 27). However, the cellular context and signals that determine their timing of activation are not well understood.

To address these questions, we studied the murine fetal liver, an erythropoietic tissue rich in erythroid progenitors. Our recent work using this model system showed that the transition from the self-renewing CFUe to ETD in vivo coincides with the upregulation of the cell surface marker CD71, making it accessible to molecular study (23). We found that ETD is activated during early S phase, during a rapid cell fate switch that comprises a number of simultaneous commitment events, including the onset of dependence on the hormone erythropoietin (Epo) for survival, chromatin reconfiguration (23) and an unusual process of global DNA demethylation (28). These commitment events are dependent on S phase progression, since their induction can be reversibly prevented by reversibly arresting DNA replication (23).

The present study explored the requirement for S phase progression during this cell fate switch, by asking whether S phase at the time of the switch might differ from S phase in preceding cycles. We previously noted that the switch to ETD coincides with an increase in intra-S phase DNA synthesis rate, possibly indicating a shorter S phase (23, 28). While the length of the G1 phase is well documented as a regulatory target of growth factors and differentiation signals (4, 7), much less is known regarding the regulation of S phase length in mammals. By contrast, the well-studied post-fertilization cleavage cycles of model organisms such as frog and Drosophila last only minutes, and comprise an extremely short S phase; S phase lengthens abruptly at the mid-blastula transition (29-32). This dramatic change in S phase length is the result of altered firing efficiency of origins of replication, which transition from synchronous, efficient firing during the short cleavage cycles, to asynchronous and less efficient firing at the mid-blastula transition (30, 33). Although far less is known regarding the possible regulation of S phase length during mammalian development, older reports have noted transient S phase shortening during key cell fate decisions, including shortening of S phase to <3 hours in epiblasts of mouse and rat embryos as they transition through the primitive streak and become either endoderm or mesoderm (34-36). The relevance of altered S phase duration to mammalian differentiation, and the underlying mechanisms, are not known.

As shown below, the transition from CFUe to ETD entails a transient shortening of S phase, in part regulated by p57$^{KIP2}$, a member of the Cip/Kip family of cyclin-dependent kinase (CDK) inhibitors (CDKI) (37-40). Without wishing to be bound by theory, it appears that p57$^{KIP2}$ prolongs the duration of S phase in self-renewing progenitors, a function essential for their viability both in vivo and in vitro. Remarkably, the mechanism controlling S phase duration does not involve altered firing of replication origins, but instead, altered speed of replication forks. In the presence of p57$^{KIP2}$, replication forks are slower; its down-regulation with activation of the ETD results in globally faster forks.

Unexpectedly and counter-intuitively, we discovered that CDK inhibition is essential for, and promotes, the self-renewal of early erythroid progenitors in vivo and in vitro. Thus, CDK inhibiting drugs can be used to enhance self-renewal of hematopoietic stem and progenitor cells, both in vitro and in vivo. This may be applied in vitro, where it may be of translational relevance in a number of scenarios, including:

(1) Ex vivo expansion of human early erythroid progenitors from early, CD34+ progenitors, and (2) Ex vivo expansion of human hematopoietic stem cells (HSCs), from either bone-marrow or cord blood.

In addition, CDKI drugs can be used in vivo as treatments in situations where HSCs fail to self-renew, particularly in bone-marrow failure syndromes secondary to DNA repair deficits, such as in Fanconi Anemia.

Cyclin-Dependent Kinases (CDKs)

Cyclin-Dependent Kinases (CDKs) are constitutively expressed serine/threonine kinases, which become active when associated with a cyclin molecule (Whittaker et al., Pharmacol Ther. 2017; 173:83-105; Lim and Kaldis, Development. 2013; 140(15):3079-3093). There are 21 CDKs encoded by the human genome, regulating a wide variety of functions associated with cell growth and proliferation. A well studied subset of these is directly responsible for progression of the cell cycle. Thus, CDK4 and CDK6 are 'G1' cyclins. Mitogenic stimuli such as extracellular growth factors stimulate induction of their cyclin activators, cyclins D1, D2 and D3; the activated cyclin D/CDK4 or Cylin D/CDK6 complexes then phosphorylate the retinoblastoma protein (pRB), an inhibitor of cell growth. Rb is further 'hyperphosphorylated' by Cyclin E/CDK2. These G1 phase phosphorylation events inactivate Rb, allowing cells to pass through the 'restriction point', which commits them to cell replication (Weinberg, Cell. 1995; 81(3):323-330).

CDK2 continues to regulate progression of the cycle, first in late G1/early S phase, in association with cyclin E, and then in S-phase, in association with cyclin A; cyclin A/CDK1 and cyclin B/CDK1 regulate transitions through G2 and M. CDK2 and CDK1 have multiple putative targets in S phase, some of which have been shown to be critical for the process of DNA replication, including targets whose phosphorylation is essential to the activation of origins of replication (Zegerman et al., Nature. 2007; 445(7125):281-285; Loog et al., Nature. 2005; 434(7029):104-108).

Cell cycle dysregulation is one of the hallmarks of cancer; the pRB pathway is frequently if not always implicated (Hanahan and Weinberg, Cell. 2000; 100(1):57-70). CDK inhibitors (CDKIs) are a group of proteins that associate with cyclin/CDK complexes and inhibit their activity. They belong to two principal families: Ink4, comprising p16$^{ink4a}$, p15$^{ink4b}$, p18$^{ink5c}$ and p19$^{ink4d}$; and the Cip/Kip family, comprising p21$^{Cip1}$, p27$^{KIP1}$ and p57$^{KIP2}$ [7]. Given their inhibitory action on cell cycle progression, most if not all these proteins have documented tumor suppressor functions, and their expression is often low or lost in a variety of cancers.

Several CDK inhibitory drugs have been developed, which inhibit cell cycle progression, and are in various stages of translational application as cancer therapeutic agents; the drugs vary in their selectivity for the various cellular CDK proteins (Whittaker et al., Pharmacol Ther. 2017; 173:83-105; Santo et al., Semin Oncol. 2015; 42(6): 788-800; Roskoski, Pharmacol Res. 2016; 107:249-275). A selective CDK4/CDK6 inhibitor, Palbociclib, is now approved for the treatment of ER+/HER2− advanced breast cancer (Whittaker et al., Pharmacol Ther. 2017; 173:83-105). Other CDK inhibitors are known in the art, including those shown in Table 1. In the present methods, inhibitors of CDK2 are preferred.

TABLE 1

Cyclin-Dependent Protein Kinase Inhibitors

| Name | Activity |
|---|---|
| A-674563 | Akt1/CDK2 inhibitor |
| Aminopurvalanol A | Cyclin-dependent kinase inhibitor |
| AZD 5438 | Potent cyclin-dependent kinase (CDK) 1, 2 and 9 inhibitor |
| BMS 265246 | Potent CDK1/2 inhibitor |
| CGP 60474 | Potent dual CDK1/CDK2 inhibitor |
| CYC065 | CDK 2, 5, 9 inhibitor |
| CYC202 (Seliciclib) | CDK 2, 7, 9 inhibitor |

TABLE 1-continued

Cyclin-Dependent Protein Kinase Inhibitors

| Name | Activity |
| --- | --- |
| Flavopiridol hydrochloride | Cyclin-dependent kinase inhibitor |
| GW8510 | CDK2 inhibitor |
| 10Z-Hymenialdisine | Pan kinase inhibitor; potently inhibits CDK1, CDK2, CDK3 and CDK5 |
| Indirubin-3'-oxime | Cyclin-dependent kinase inhibitor. Also inhibits other protein kinases |
| Kenpaullone | Potent cyclin-dependent kinase inhibitor. Also inhibits GSK-3 |
| NSC 663284 | Cdc25 phosphatase inhibitor; blocks CDK1 and CDK2 activation |
| NSC 693868 | CDK inhibitor. Also inhibits GSK-3 |
| NU 2058 | CDK1 and CDK2 inhibitor |
| NU 6140 | Cyclin-dependent kinase 2 (CDK2) inhibitor |
| Olomoucine | Cyclin-dependent kinase inhibitor |
| [Ala92]-p16 (84-103) | Cyclin-dependent kinase inhibitor |
| Purvalanol A | Cyclin-dependent kinase inhibitor |
| Purvalanol B | Cyclin-dependent kinase inhibitor |
| Roscovitine | Potent, selective cyclin-dependent kinase inhibitor (CDK2, 5, 1, 7, 9) |
| SC-221409 | Potent CDK2 inhibitor |
| SCH 727965 | CDK 9, 1, 2, 5 inhbitor |
| SNS 032, BMS-387032 | Potent CDK2, CDK7 and CDK9 inhibitor |
| SU 9516 | Potent CDK2 inhibitor |
| Dinaciclib | CDK 1, 2, 5, 9 |
| TG02, SB1317 | CDKs 1, 2, 7, 9/JAK2/FLT3 |
| LDC4297 | CDK7 |
| UCN-01, 7 hydroxystaurosporine | CDK1/2 inhibitor |

Other small molecule CDK inhibitors are known in the art, including those described in Whittaker et al., Pharmacology & Therapeutics 173 (2017) 83-105; Santo et al., Semin Oncol. 2015; 42(6):788-800; Roskoski, Pharmacol Res. 2016; 107:249-275; Hsieh et al., Cell Death Discovery volume 2, Article number: 16027 (2016) doi:10.1038/cddiscovery.2016.27; and Mariaule and Belmont, Molecules 19:14366-14382 (2014). In some embodiments, the CDK inhibitor inhibits CDK1 and/or CDK2, and preferably does not inhibit CDK4.

Ex Vivo Stem Cell Expansion Erythroid Cells and Hematopoietic Stem Cells

Erythroid progenitors are generated from earlier, multipotential and oligopotential hematopoietic progenitors. They undergo a limited number of self-renewal cell divisions, before activating the erythroid transcriptional program. This results in erythroid gene expression and morphological changes over the course of 3 to 5 maturational cell divisions, a developmental phase known as erythroid terminal differentiation (ETD) that ends with enucleation and the formation of new red cells.

Pre-ETD erythroid progenitors are divided into later-stage erythroid progenitor cells and earlier erythroid progenitor cells, known as colony-forming unit-erythroid (CFU-e) and burst-forming units-erythroid (BFU-e) respectively, based on their colony-forming potential in vitro. The self-renewal potential of pre-ETD erythroid progenitors can be enhanced in vitro in the presence of glucocorticoids such as dexamethasone (von Lindern et al., Blood. 1999; 94(2):550-559). This has led to the development of in vitro systems that aim to expand erythroid progenitors for both research and translational purposes. The mechanism of action of glucocorticoids is not clear, and is an active area of research (see, e.g., Zhang et al., Nature. 2013; 499(7456):92-96; Flygare et al., Blood. 2011; 117(12):3435-3444).

As shown herein, CFU-e progenitors unexpectedly express CDKI p57$^{KIP2}$ during S phase of the cycle. This protein was believed to regulate the transition from G1 to S phase, and was not previously known to have an intra-S phase function. The transition from a self-renewal state to ETD coincided with rapid downregulation of p57$^{KIP2}$, and with speeding up of the cell cycle, including S phase shortening. Further, we showed that mechanistically, p57$^{KIP2}$ was slowing S phase in self-renewing progenitors by globally slowing the speed of replication forks.

We found that p57$^{KIP2}$-deficient CFU-e in vivo and in vitro undergo cell death, in part as a result of replication stress, since their S phase cells have significantly higher levels of phospho-H2AX, a modification that is often associated with DNA damage. We therefore suggest that a key function of CDK inhibition by p57$^{KIP2}$ in early erythroid progenitors is the slowing of replication forks, a function that promotes cell viability by reducing replication stress. Of note, other early hematopoietic cells including HSCs also express p57$^{KIP2}$, where it may exert a similar protective function against replication stress.

In vitro, cell death in the p57$^{KIP2}$-deficient CFUe resulted in their failure to undergo self-renewal in the presence of dexamethasone, unlike CFU-e from wild-type littermate embryos (FIG. 5D).

We were able to rescue the self-renewal of p57$^{KIP2}$-deficient CFU-e progenitors in vitro, by re-expressing p57$^{KIP2}$ in these cells (FIG. 5H). We were also able to rescue the self-renewal of p57$^{KIP2}$-deficient CFU-e progenitors by adding to the culture low concentrations of the drug roscovitine, a CDK inhibitor that is relatively more specific for CDK2 (an S phase CDK) than CDK4/CDK6 (FIG. 5I). This shows that CDK inhibition by p57$^{KIP2}$ is the principal function it exerts in preserving the viability of CFUe progenitors during self-renewal.

We confirmed that the p57$^{KIP2}$-deficient cells whose expansion was amplified by the addition of roscovitine (FIG. 5I) were indeed self-renewing CFUe progenitors, by plating these progenitors in semi-solid medium and showing that they retained the same potential for the formation of CFU-e colonies, per number of viable cells plated, as did untreated cells (FIG. 12B). Therefore, the expansion in viable cell numbers in the presence of roscovitine reflects a genuine increase in the number of progenitors with CFU-e potential, as a result of improved CFU-e self-renewal.

Figure 5J:
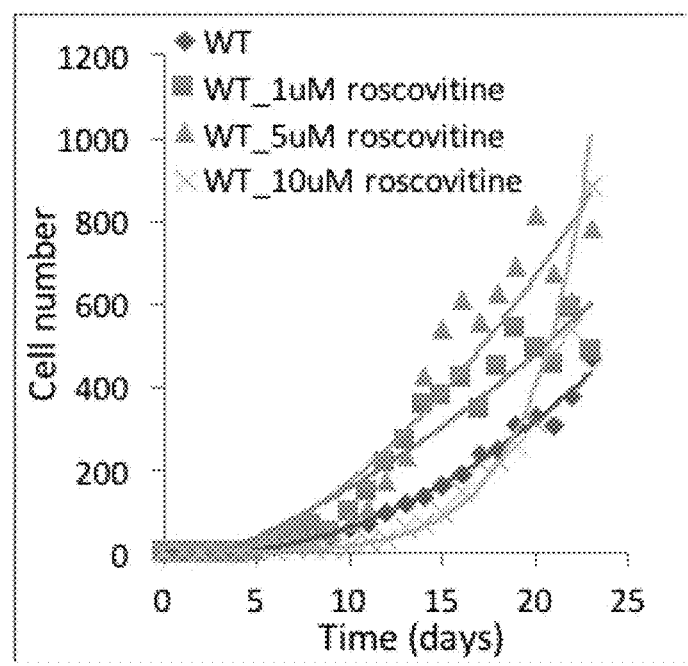

We also found that addition of roscovitine enhanced the amplification of wild-type CFU-e (FIGS. 5I-J).

The present methods include culturing stem cells, e.g., human stem cells, e.g., hematopoietic stem cells, in the presence of an effective amount of a CDK inhibitor.

Methods of amplifying early erythroid progenitors (e.g., CFU-e, typically CD45$^+$GPA$^-$IL-3R$^-$CD34$^-$CD36$^+$CD71$^{high}$), e.g., from early, CD34+ progenitors (e.g., BFU-e, typically CD45$^+$GPA$^-$IL-3R$^-$CD34$^+$CD36$^-$CD71$^{low}$) are also known in the art. See, e.g., Wognum, "Hematopoeitic Stem and Progenitor Cells," document #29068, version 6.0.0 April 2015, available at stemcell.com/media/files/minireview/MR29068-Hematopoietic_Stem_and_Progenitor_Cells.pdf; Dexter et al. J Cell Physiol 91: 335-344, 1977; Gartner and Kaplan, Proc Natl Acad Sci USA 77: 4756-4759, 1980; Whitlock and Witte, Proc Natl Acad Sci USA 79: 3608-3612, 1982; Miller et al., Blood 80: 2182-2187, 1992; Cho and Muller-Sieburg, Exp Hematol 28: 1080-1086, 2000; Miller and Eaves, Methods Mol Med 63: 123-141, 2002; Dolznig et al., "Expansion and Differentiation of Immature Mouse and Human Hematopoietic Progenitors," From: *Methods in Molecular Medicine, Vol. 105: Developmental Hematopoiesis: Methods and Protocols*. M. H. Baron, Ed. Humana Press Inc., Totowa, N.J., pp 323-343 (2005). The methods can include maintaining the cells, e.g., a starting population of cells, in media comprising erythropoietin (EPO) and one or more other cytokines, particularly Stem Cell Factor (SCF), IL-3, IL-6, and granulocyte/macrophage colony-stimulating factor (GM-CSF), e.g., for initial cell division and differentiation, while CFU-e should be cultured in the presence of EPO (see, e.g., Wognum, 2015). Typically, glucocorticoids such as hydrocortisone or dexamethasone are also added (see, e.g. Dolznig, Methods in Molecular Medicine 105:323-344 2005). The starting population of cells can be obtained, e.g., from bone marrow, mobilized peripheral blood mononuclear cells, or umbilical cord blood, using methods known in the art. In some embodiments, specific cells are enriched for in the starting population, e.g., using cell sorting (e.g., FACS or immunoaffinity isolation using magnetic beads, e.g., with antibodies that bind to CD34) to enrich for CD34+ cells, or using density gradient purification, e.g., using a ficoll gradient to provide an enriched population. See, e.g., Li et al, Blood 2014. 124:3636-3645 (Isolation of human BFU-E and CFU-E).

The expanded erythroid progenitors can be used, e.g., for generating transfusable red blood cells in vitro (see, e.g., Migliaccio et al., Cell Stem Cell. 2012; 10(2):115-119; Giarratana et al., Blood. 2011; 118(19):5071-5079 (e.g., using erythroid differentiation medium (EDM) supplemented with EPO)). These may be particularly useful for rare blood types, and for the application of gene therapy for blood genetic diseases, e.g., hemoglobinopathies such as sickle cell anemia or β-thalassemia.

The present methods can also be used to provide expanded population of HSC, e.g., human HSC, e.g., Lin$^-$CD34$^+$CD38$^-$CD45RA$^-$CD49f$^+$CD90$^-$ cells. The expansion of HSCs in vitro remains a serious challenge, in spite of efforts in recent years to improve growth conditions and a number of novel agents (see, e.g., Walasek et al., Annals of the New York Academy of Sciences. 2012; 1266(1):138-150). Expansion of HSCs from cord blood is particularly desirable for allogeneic stem cell transplantation following myeloablative treatment (see, e.g., Cutler et al., Blood. 2013; 122(17):3074-3081). In vitro culture of HSCs is required in gene therapy protocols, where HSCs are transduced with a lentiviral vector while in culture, and need to survive culture conditions for long enough to ascertain that the required transduced gene is expressed and that integration site is safe; the transduced HSCs are then used in autologous transplantation (see, e.g., Biffi et al., Science. 2013; 341(6148)). HSC culture is also critical for the development of gene editing therapies, e.g., wherein gene-edited HSC are used in in the treatment of genetic diseases, e.g., hemoglobinopathies (see, e.g., Genovese et al., Nature. 2014; 510(7504):235-240).

Methods for culturing human HSCs from either bone marrow, mobilized peripheral blood mononuclear cells, or umbilical cord blood are known in the art and include maintaining the cells, e.g., a starting population of cells, in suitable conditions, e.g., comprising one or more cytokines, e.g., stem cell factor (SCF), FLT3 ligand (FL), interleukin-3 (IL-3), granulocyte-macrophage colony-stimulating factor (GM-CSF) and thrombopoietin (TPO), e.g., as described in Flores-Guzmán et al., Cells Translational Medicine 2013; 2:830-838; Dahlberg et al., Blood. 2011; 117(23):6083-6090; Douay and Andreu, Transfusion Medicine Reviews, Vol 21, No 2 (April), 2007: pp 91-100). In some embodiments, the cells are cultured in presence of one or more of five growth factors: SCF, IL-3, IL-6, G-CSF, and Flt3L. See, e.g., Knapp et al., Stem Cell Reports 8:152-162 (2017). In some embodiments, specific cells are enriched for in the starting population, e.g., using cell sorting (e.g., FACS or immunoaffinity isolation using magnetic beads, e.g., with one or more antibodies that bind to CD34, C-KIT, TIE, and/or CD133/AC133, optionally excluding cells that express CD38, LIN, and CD45RA) to enrich for HSC. See, e.g., Yokota T, Oritani K, Butz S, Ewers S, Vestweber D, Kanakura Y. "Markers for Hematopoietic Stem Cells: Histories and Recent Achievements." In: Pelayo R, et al., editors. *Advances in Hematopoietic Stem Cell Research.* Mexico City: InTech; 2012. pp. 77-88.

The cells can be provided in a composition that is ready for administration to a subject. The methods can include administering the progenitors, or differentiated cells derived therefrom, into a subject in need thereof.

Methods of Treatment

The CDK inhibitors can also be used in vivo as treatment in subjects who have anemia, or whose HSCs fail to self-renew, particularly in bone marrow failure syndromes (BMFSs) secondary to DNA repair deficits, as in Fanconi Anemia.

BMFSs are disorders that can include loss or dearth of only a single cell type (e.g., erythroid, myeloid, or megakaryocytic cytopenia, as seen in congenital neutropenia, including Kostmann syndrome; Diamond-Blackfan anemia; Shwachman-Diamond syndrome; congenital amegakaryocytic thrombocytopenia (CAMT); or thrombocytopenia absent radii (TAR) syndrome) or as pancytopenia (e.g., hypoplastic marrow or aplastic marrow, as seen in Fanconi anemia and dyskeratosis congenita). Although the list above includes inherited BMFSs, the condition can also be acquired. Acquired bone marrow failure syndromes, e.g., aplastic anemia; anemia that is idiopathic or caused by exposure toxins, drugs, chemicals, radiation, viral infection, malnutrition or vitamin deficiencies including vitamins B12 and folate; or myelodysplastic syndrome (MDS). See, e.g., Dokal and Vulliamy, Inherited aplastic anaemias/bone marrow failure syndromes. Blood Rev. 2008 May. 22(3):141-53; Alter, "Inherited bone marrow failure syndromes." Nathan D G, Orkin S H, Look A T, Ginsburg D, eds. *Nathan and Oski's Hematology of Infancy and Childhood.* 6th Edition. Philadelphia, Pa.: WB Saunders; 2003. 280-365; Alter, "Inherited forms of aplastic anemia: the inherited bone marrow failure syndromes (IBMFS)". Burg F D, Ingelfinger J R, Polin R A, Gershon A A, eds. *Gellis and Kagan's Current Pediatric Therapy.* Philadelphia, Pa.: Elsevier; 2005; Alter, Bone marrow failure syndromes. Clin Lab Med. 1999 Mar. 19(1):113-33. The methods include administering a composition comprising a therapeutically effective amount of a CDK inhibitor, to a subject who is in need of, or who has been determined to be in need of (e.g., diagnosed with a BMFS using known methods), such treatment.

As used in this context, to "treat" means to ameliorate at least one symptom of BMFS or anemia. By definition BMFS or anemia results in a reduction in numbers of some or all of a subject's blood cells, as described above; thus, a treatment can result in an increase in functional hematopoietic stem cells and a return or approach to normal numbers of cells. Anemia can be diagnosed using methods known in the art, e.g., based on having a lower than normal hemoglobin concentration in blood; the normal range is 12.0-16.0 g/dl. In some embodiments, the subject has hemoglobin concentration of 10.8 g/dl, or 10 g/dl, or lower, and the treatment can result in an increase in hemoglobin concentration into the normal range.

Alternatively, the CFU-e cells produced by a method used herein can be administered to a subject in need thereof, e.g., a subject with anemia or BMFS. Methods for administering cells are known in the art. Preferably the cells are autologous, e.g., made using a method described herein from cells or tissue from the subject who is in need of treatment.

EXAMPLES

The invention is further described in the following examples, which do not limit the scope of the invention described in the claims.

Example 1. Global Increase in Replication Fork Speed During a p57KIP2-Regulated Erythroid Cell Fate Switch Materials and Methods The following materials and methods were used in the Examples 1.1 to 1.7, below.

Mice

Female mice heterozygous for a deletion of the cdkn1c gene (B6.129S7-Cdkn1$^{ctm1Sje}$/J, Jackson laboratory stock #000664) were bred with wild type C57BL/6J mice or male cdkn1c heterozygous mice. All experiments were done with littermate p57$^{KIP2}$-deficient or wild-type control embryos. All embryos were genotyped prior to further processing of the fetal livers.

Isolation and Flow Cytometric Analysis of Erythroid Progenitors

Fetal livers were harvested from mid-gestation mouse embryos (E12.5-13.5), were mechanically dissociated, labeled with antibodies to CD71 and Ter119 and with lineage markers, and sorted by flow cytometry as described (23, 81). Cells were sorted on a FACSAria (BD Biosciences) using a 100 µm nozzle. Flow cytometric analysis was done on an LSRII (BD Biosciences) cytometer. FACS data was analyzed using the FlowJo software (Tree Star Inc., CA). In some experiments, S0 cells were isolated from fetal liver cells using EasySep magnetic beads (StemCell Technologies) by negative sorting for CD71, Ter119, Gr1, Mac1 and CD41.

Antibodies Used in Flow Cytometric and EasySep Purifications:

PE/Cy7 rat anti-mouse CD71 (RI7217) (BioLegend 113812)

PE rat anti-mouse Ter119 (Ter119) (BD Biosciences 553673)

APC rat anti-mouse Ter119 (Ter119) (BD Biosciences 557909)

biotin rat anti-mouse CD71 (C2) (BD Biosciences 557416)

biotin rat anti-mouse Ter119 (BD Biosciences 553672)

biotin rat anti-mouse Ly-6G and Ly-6C/Gr1 (RB6-8C5) (BD Biosciences 553125)

biotin rat anti-mouse CD11b/Mac1 (M1/70) (BD Biosciences 557395)

biotin rat anti-mouse CD41 (MWReg30) (Thermo Scientific MA1-82655)

FITC Rat Anti-Mouse Ly-6G and Ly-6C/Gr1 (RB6-8C5) (BD Biosciences 553127)

FITC rat anti-mouse CD11b/Mac1 (M1/70) (BD Biosciences 557396)

FITC rat anti-mouse CD41 (MWReg30) (BD Biosciences 553848)

FITC rat anti-mouse CD45R/B220 (RA3-6B2) (BD Biosciences 553087)

FITC hamster anti-mouse CD3e (145-2C11) (BD Biosciences 553061)

PE Annexin V (BD Biosciences 556421)

Alexa Fluor 488 mouse anti-H2AX (pS139) (N1-431) (BD Biosciences 560445)

Isolation of G1 and S Phase Cells from S0 and S1 Erythroid Subsets

E13.5 fetal livers were harvested from wild type BALB/cJ mice (Jackson laboratory stock #000651), were mechanically dissociated, resuspended at $10^6$ cells/ml, and maintained at 37° C. for 15 min with IMDM (L-glutamine, 25 mM HEPES) (Gibco), 20% fetal calf serum (Gibco, HyClone), 100 U/ml penicillin/streptomycin (Invitrogen), $10^{-4}$M β-mercapthoethanol (Sigma) and 2 U/ml Epo. Hoechst 33342 (5 µg/ml, Invitrogen H3570) was added for 40 minutes at 37° C. Cells were collected, washed, and labeled with antibodies to CD71, Ter119 and lineage markers and with the cell viability dye 7AAD (BD Biosciences 559925). Cells were then sorted on a FACSAria (BD Biosciences). G1 and S phase cells in the S0 and S1 subsets were gated based on DNA content, as reflected by Hoechst fluorescence.

Cell Cycle Analysis

Pregnant female mice at mid-gestation were injected with BrdU (200 µl of 10 mg/ml stock in PBS) intra-peritoneally. E13.5 embryos were harvested 30 min later. To determine DNA replication rate in vitro, cells were pulsed with a final concentration of 33 uM BrdU for 30 minutes. Cells were immediately labeled with LIVE/DEAD kit (Invitrogen L23105), fixed and permeabilized. Erythroid subsets were identified using anti-CD71 (BD Biosciences 113812) and anti-Ter119 (BD Biosciences 553673). BrdU incorporation and DNA content were detected by biotin-conjugated anti-BrdU (Abcam ab171059), streptavidin-conjugated APC (Invitrogen S868) and 7AAD (BD Biosciences 559925).

Measurement of S Phase Duration

Pregnant female mice were injected intraperitoneally with 200 µl of EdU (3.3 mol/25 g mouse), followed either 1 or 2 hours later with BrdU (3.3 mmol/25 g mouse), and sacrificed 20 minutes following the second injection. Fetal livers were labeled with lineage markers, Ter119 and CD71, and S0 and S1 cells were sorted. Sorted subsets were then labeled with LIVE/DEAD kit (Invitrogen L23105), fixed in 70% ethanol, denatured in 4M hydrocholoric acid, and washed in phosphate/citric buffer. EdU incorporation was detected using Click-iT EdU Alexa Fluor 488 Flow Cytometry Assay kit (Invitrogen C10425) and BrdU incorporation was detected using Alexa Fluor 647 mouse anti-BrdU (Invitrogen B35133).

In Vitro CFUe Expansion Cultures (51, 82)

To isolate Ter119-negative cells, fresh fetal liver cells were stained with biotin-conjugated anti-Ter119 (BD Biosciences 553672) at 1:100, followed by EasySep magnetic separation (StemCell Technologies). Cells were grown in Stem-Pro-34 serum free medium supplemented with nutrient supplement (Invitrogen), 1 µM dexamethasone (Sigma), 100 ng/ml SCF (PeproTech), 40 ng/ml IGF1 (PeproTech), 2 U/ml Epo, 100 U/ml penicillin/streptomycin (Invitrogen) and 2 mM L-glutamine (Invitrogen). Cells were maintained at $2\times10^6$ cells/ml, and supplemented daily with fresh medium and growth factors. To test the effect of roscovitine on p57$^{KIP2}$-/- fetal liver cells in expansion culture, cells were grown and maintained as described above with the additional supplemented daily of 0.5 µM roscovitine (EMD Millipore 557360). To switch to differentiation medium, after being maintained in expansion medium for 4 to 5 days, Ter119-negative cells were isolated again using EasySep magnetic beads (StemCell Technologies). Cells were then transferred to IMDM (L-glutamine, 25 mM HEPES) (Gibco), 20% fetal calf serum (Gibco, HyClone), 100 U/ml penicillin/streptomycin (Invitrogen), $10^4$ M β-mercaptoethanol (Sigma) and 2 U/ml Epo.

Retroviral Transduction with p57 Constructs

Retroviral constructs were generated in the MSCV-IREShCD4 vector backbone as described (23). p57 mutant (p57T329A) was previously described (23). CDK-binding mutants defective p57W50G and p57F52A/F54A were generated using PCR with the following primers: CCAGAACCGCGGGGACTTCAACTTCC (SEQ ID NO:1) and TCCTCGGCGTTCAGCTCG (SEQ ID NO:2) (for p57W50G), and CGCCCAGCAGGATGTGCCTCTTC (SEQ ID NO:3) and TTGGCGTCCCAGCGGTTCTGGTC (SEQ ID NO:4) (for p57F52A/F54A). The entire open reading frame was sequenced to verify correct mutagenesis. Viral supernatants were prepared as described (23). S0 cells were transduced by spin infection at 2,000 rpm, 30° C. for 1 h in fibronectin-coated dishes supplemented with 4 µg/ml of polybrene (Sigma). Cells were incubated with 100 ng/ml SCF and 10 ng/ml IL3 (PeproTech) overnight before cell cycle analysis.

Knockdown Experiments

A short hairpin RNA targeting $p57^{KIP2}$ (clone SM22685-D-5 V2MM_81921) was subcloned into LMP microRNA-adapted retroviral vector containing an "IRES-GFP" reporter (Open Biosystems, Huntsville, Ala.). Similarly, a non-silencing negative control shRNA (RHS4971, Open Biosystems) that is processed by the endogenous RNAi pathway but will not target any mRNA sequence in mammals was subcloned into LMP. Sorted S0 cells were transduced with retroviral vectors, expressing short hairpin RNA for 16 h in the presence of SCF and IL3. Cells were then cultured for Epo±Dex for 20 to 72 hours, before cell cycle analysis.

Quantitative RT-PCR

Total RNA was isolated from fetal liver cells using the AllPrep DNA/RNA Micro Kit and RNeasy Micro Kit (Qiagen), and quantified by Quant-iT RiboGreen RNA reagent kit (Thermo Scientific). The SuperScript III first-strand synthesis system (Invitrogen) was used in reverse transcription. Quantitative PCR was conducted in the ABI 7300 sequence detection system with TaqMan reagents and TagMan MGB probes (Applied Biosystems).

Taqman Probes:

β-actin (Mm02619580_g1), β-globin (Mm01611268_g1), $p21^{CIP1}$ (Mm00432448_m1), $p27^{KIP1}$ (Mm00438168_m1), $p57^{KIP2}$ (Mm01272135_g1)

Western Blot Analysis

Sorted fetal liver cells, or fetal liver cells from expansion and differentiation cultures were incubated in lysis buffer (1% NP40, 50 mM Tris pH 7.4, 150 mM NaCl, 1 mM EDTA, 10% glycerol supplemented with protease inhibitors) and rotated at 4° C. for 30 minutes. Supernatants were prepared by centrifugation at 4° C. for 15 minutes and quantified by the BCA Protein Assay Kit (Pierce). Protein electrophoresis was carried out using the NuPAGE Novex Bis-Tris Gel System and the Bolt Bis-Tris Plus Gel System (Invitrogen). PVDF membranes were probed with antibodies against $p57^{KIP2}$ (Abcam ab75974), β-actin (Abcam ab8227), $p21^{CIP1}$ (Abcam ab109199), $p27^{KIP1}$ (Cell Signaling Technology 3698) and α-globin (Abcam ab92492). Target protein bands were detected by ChemiDoc XRS+ system (BIO-RAD) and quantified using Image Lab software (BIO-RAD). Negative and positive controls were used in all western blots, consisting of lysates of either 3T3 or 293T cells, transduced with either 'empty vector' or with retroviral vector expressing the relevant test protein.

DNA Combing

Freshly harvested fetal liver cells were allowed to recover in Epo-containing medium at 37° C. for 4 hours. They were then pulsed with IdU (25 µM) for 10 minutes, followed immediately, without intervening washes, by a CldU pulse (200 µM) for 20 minutes. Cells were labeled with CD71 and Ter119 antibodies as described above, and subsets S0 and S1 were sorted by flow cytometry. The sorted cells were washed in PBS and embedded in agarose plugs (0.75% Low Melt agarose (BIO-RAD). Plugs were incubated in 0.2 mg/ml proteinase K (Roche) solution at 37° C. for 48 hours. After extensive washing, agarose plugs were melted and digested with β-agarase. Genomic DNA was gently resuspended in 0.2 M IVIES buffer, pH 5.4, and combed on silanized coverslips using the Molecular Combing System (Genomic Vision, Bagneux, France). Combed DNA was denatured in 2 M hydrochloric acid, and labeled with rat anti-BrdU (Abcam ab6326) and Alexa Fluor 594 goat anti-rat IgG (Life Technologies A11007) to identify IdU tracks; with mouse anti-BrdU (BD Biosciences 347580) and Alexa Fluor 488 goat anti-mouse IgG (Invitrogen A11029) to identify CldU tracks; and with anti-single stranded DNA rabbit IgG (Immuno-Biological Laboratories CO., Ltd. 18731), biotin-conjugated goat anti-rabbit IgG (BD Biosciences 550338), BV421 streptavidin (BioLegend 405226) and BV421 anti-human IgG (BioLegend 409317), to identify single stranded DNA fibers.

Fluorescence microscopy was carried out on a Zeiss Axioskop 40 fluorescence microscope. Separate exposures were taken for red, blue and green fluorescence for each field, and merged using GNU Image Manipulation Program (GIMP). Up to 40 consecutive fields were photographed and merged digitally for each of the final image files that were then analyzed by a scientist that was blinded to sample identity. DNA track lengths were measured using GIMP. IdU track lengths were tracks that labeled only with green fluorescence. Examples of original fluorescence images are shown in FIG. 19.

Cell Cycle and γH2AX Analysis In Vivo

Pregnant female mice were injected intraperitoneally with 200 µl of BrdU (10 mg/ml). Mice were sacrificed at 30 min post injection. Fetal livers were fixed and permeabilized, digested with DNaseI, labeled for BrdU incorporation, non-erythroid lineage markers and cell surface markers CD71 and Ter119, and analyzed by flow cytometry. Where indicated, cells were labeled with antibodies against γH2AX prior to the DNaseI digestion.

Statistical Analysis

One-way ANOVA was used to compare measured parameters from the 3 different genotypes (wild type, $p57^{KIP2}+/-^m$, $p57^{KIP2}-/-$), using the GraphPad Prism 7.0 software. Statistical significance of the DNA combing data was assessed using Student t test. The Mann Whitney test was used for non-normally-distributed datasets.

Example 1.1—Activation of Erythroid Terminal Differentiation Coincides with S Phase Shortening To study the activation of ETD in vivo we divided erythroid-lineage cells in the fetal liver into six sequential developmental subsets, Subsets 0 to 5 (S0 to S5), based on expression of cell surface markers CD71 and Ter119 (FIG. 1A, FIG. 7A) (23, 41, 42). Subsets S0 and S1 contain progenitors with CFUe colony forming potential (giving rise to colonies of 16-32 red cells within 72 hours), whereas subsets S2 to S5 contain maturing erythroblasts undergoing ETD, marked by expression of the erythroid cell surface marker Ter119 (23). We have previously shown that the switch to ETD in CFUe progenitors involves a series of events that are synchronized with the cell cycle and that can be followed in an orderly manner by observing changes in CD71 and Ter119 expression (23). Thus, CFUe progenitors undergo a limited number of self-renewal divisions while in the S0 subset, including the last cell division of the CFUe progenitor stage. The progeny of this last cell division (colored purple, FIG. 1A) undergo a sharp increase in cell surface CD71 when in early S phase of the cycle, transitioning into the S1 subset. This transition, which depends on S phase progression, marks the switch to ETD and the onset of Epo dependence. The ensuing induction of erythroid genes, including expression of cell-surface marker Ter119 and transition into the S2 subset, take place around the time that these cells undergo the next mitosis. Therefore, the S1 subset contains largely S phase cells during a rapid transition from CFUe to ETD (FIG. 1A) (23).

Figures 7A, 7B, 7C, 7D:
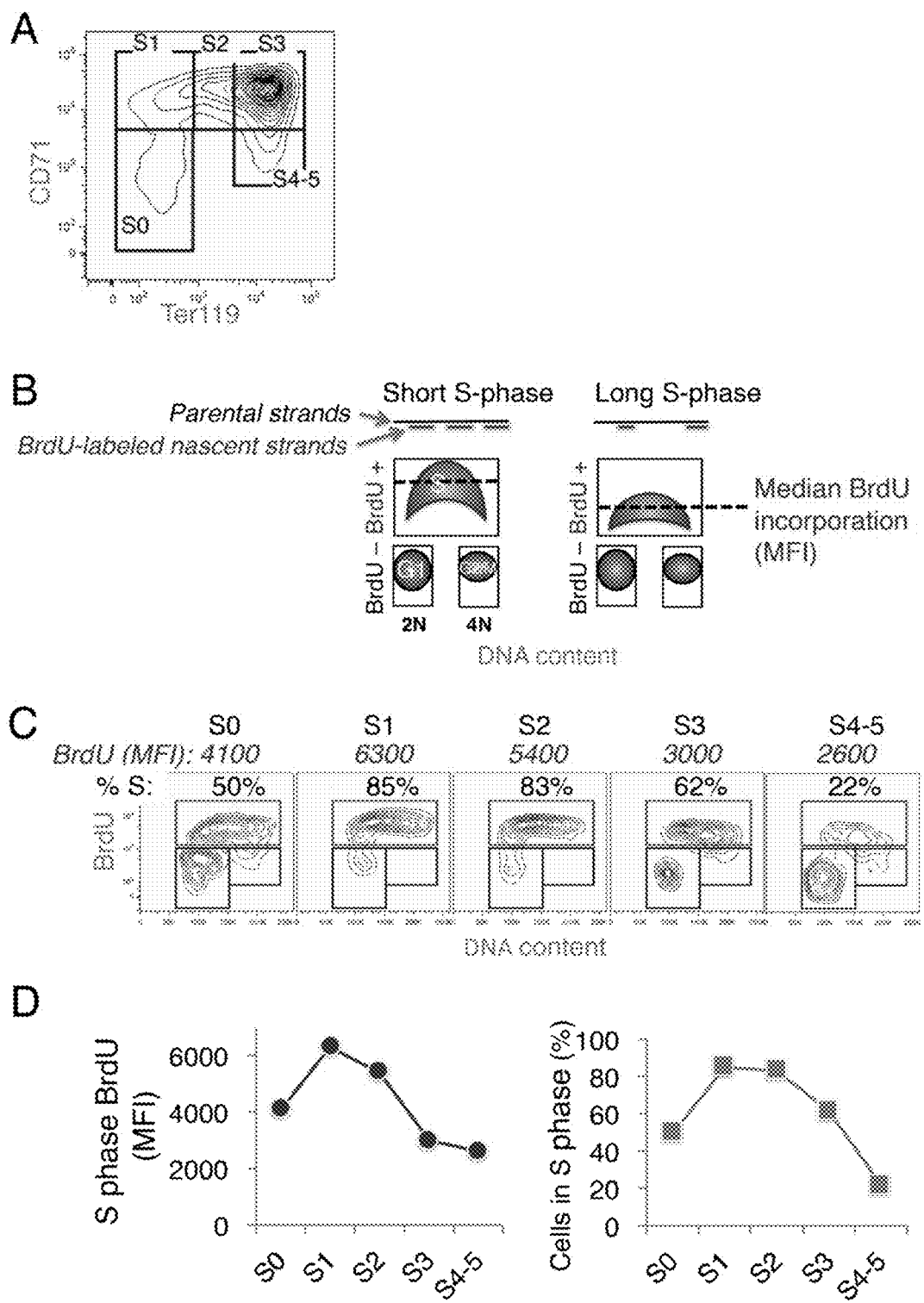

To analyze the cell cycle characteristics of CFUe progenitors during this transition, we injected pregnant female mice with the nucleoside analog bromodeoxyuridine (BrdU), and harvested embryos 30 minutes post injection. The cartoon in FIG. 7B illustrates two distinct parameters of replication that may be obtained from this experiment. First, the number of cells in S phase is measured based on their incorporation of BrdU into replicating DNA (BrdU+ cells). Second, the rate of BrdU incorporation into S phase cells, measured as the BrdU median fluorescence intensity within the S phase gate (dashed black line, FIG. 7B), indicates the intra-S phase rate of DNA synthesis (43, 44). We found that, in spite of being exposed to the same BrdU pulse in vivo, S phase cells within a single fetal liver vary substantially in their BrdU incorporation rate, depending on their stage of differentiation. Specifically, in the shown example in FIG. 7C, BrdU median fluorescence intensity (MFI) is 54% higher in S1 compared with S0 of the same fetal liver (FIG. 7C-7D). This result is consistent with our earlier data in subsets sorted from pooled fetal livers, which showed that the average BrdU incorporation rate in S1 cells is 55±13% higher than in S0 (mean±SEM of 6 independent experiments, p=0.02 (23, 28)). This result indicates a substantially faster DNA synthesis rate in S phase cells in the S1 subset, compared with S0 cells, and suggests that genome replication in S1 cells might be completed sooner, resulting in a shorter S phase (FIG. 7B).

Here we examined this possibility by using a double-nucleoside label approach (45, 46). We injected pregnant female mice sequentially with two distinct deoxynucleoside analogs of thymidine: first with a pulse of 5-ethynyl-2-deoxyuridine (EdU), followed, after an interval 'I', by a BrdU pulse (FIG. 1B-E). We explanted fetal livers immediately (20') following the second, BrdU pulse, isolated S0 and S1 cells by FACS sorting, and analyzed cells for incorporation of EdU, BrdU, or both. To calculate S phase and the cell cycle length, we measured two parameters. First, the EdU$^+$BrdU$^-$ cell fraction, which represents cells that were in S phase during the first, EdU pulse, but have exited S phase during the ensuing interval 'I'. This cell fraction is therefore proportional to the duration of 'I' (FIG. 1B). Second, we measured the fraction of cells that are BrdU+ (whether or not they are also EdU+), which corresponds to the fraction of cells in S phase just prior to embryo harvest. (Note that, because of the finite but unknown clearance time for the first, EdU pulse in vivo, cells entering S phase during the interval I continue to incorporate EdU, denoted by a hashed green line in FIG. 1B. It is therefore not possible to use the fraction of EdU+ cells as a measure of the fraction of cells in S phase.) Five independent experiments, with 'I' either 1 or 2 hours, and including one experiment in which the EdU and BrdU labels were reversed, resulted in the expected linear relationship between 7' and the fraction of cells that exited S phase ($r^2$=0.95 and 0.85 for S1 and S0, respectively, FIG. 1D). We calculated the length of the cell cycle as 15±0.3 h (mean±SE) and 5.8±0.1 h for S0 and S1 cells, respectively, suggesting a dramatic cell cycle shortening at the S0/S1 transition. S phase shortening contributed to the shortening of the cycle, decreasing by >40%, from 7.1±0.3 h in S0, to 4.1±0.2 h in S1 cells (mean±SEM), which corresponds to a 73±15% increase in intra-S phase DNA synthesis rate. This shortening is in agreement with the increased BrdU incorporation rate at the transition from S0 to S1 ((23), and FIG. 7C-D), validating the latter approach as a measure of intra-S phase DNA synthesis rate in our system. In addition to S phase shortening, G1 and G2-M phases also become substantially shorter with the switch from S0 to S1 (FIG. 1E).

These results are consistent with early reports documenting a doubling time of 6 hours for murine CFUe in vivo (24), and an extremely short S phase of 2.5 hours for rat erythroblasts (45). Here we go beyond these findings, clearly linking cell cycle and S phase shortening with a cell fate switch, from self-renewal in S0, to ETD in S1.

Example 1.2—p57$^{KIP2}$ is Expressed in S Phase, Slowing Intra-S Phase DNA Synthesis Rate To investigate the mechanism of S phase shortening in S1 cells, we compared expression of cell cycle regulators in S0 and S1. We previously found that p57$^{KIP}$ is expressed in S0, and is rapidly downregulated with the transition to S1 (23). By contrast, other members of the Cip/Kip family, p21$^{CIP1}$ and p27$^{KIP1}$, are not significantly expressed in S0 and S1 and are instead induced later, at the very end of ETD (23). p57$^{KIP2}$ was previously documented to act in the G1 phase, where it inhibits the transition from G1 to S phase (37, 38). Here we examined the cell cycle phase in which p57$^{KIP2}$ is expressed, by sorting freshly explanted S0 and S1 cells enriched for either G1 or S phase, based on their DNA content (FIG. 2A). We found that, surprisingly, the highest levels of p57$^{KIP2}$ mRNA and protein were attained in S phase of S0 cells (FIG. 2B-C). There was a significant, 50-fold decline in p57$^{KIP2}$ mRNA in phase cells between S0 and S1 (p=0.0079, Mann Whitney test), while there was no significant difference in p57$^{KIP2}$ mRNA levels between S0 and S1 cells in G1 phase of the cycle, where it was expressed at lower levels.

These findings suggested a possible S phase function for p57$^{KIP2}$. To test this, we used short hairpin (sh)RNA to target p57$^{KIP2}$ in S0 cells that were explanted and cultured in the presence of Epo and dexamethasone, conditions that promote CFUe self-renewal (47). In addition to the expected increase in the number of S phase cells, knock-down of p57$^{KIP2}$ resulted in the doubling of intra-S phase DNA synthesis rate (which increased by 2±0.29 fold, mean±SD, p=0.005) relative to cells transduced with non-silencing shRNA (FIG. 2D-E).

We also examined the effect on S phase of p57$^{KIP2}$ over-expression in S0 cells. We previously found that this led to cell cycle and differentiation arrest at the S0/S1 transition (23). Here we subdivided transduced S0 cells digitally into gates based on their expression level of p57$^{KIP2}$, as indicated by an hCD4 reporter linked through an IRES to p57$^{KIP2}$ (23) (FIG. 2F). We found that p57$^{KIP2}$ exerted dose-dependent slowing of intra-S phase DNA synthesis rate (FIG. 2F; FIG. 8). As expected, in addition, $p57^{KIP2}$ inhibited the transition from G1 to S in a dose-dependent manner (FIG. 2F). A degradation-resistant mutant of $p57^{KIP2}$, p57 T329A, was more potent in its ability to slow down intra-S phase DNA synthesis rate, while its ability to inhibit the G1 to S phase transition was comparable to wild-type $p57^{KIP2}$ (FIG. 2F). Taken together, both our knock-down and over-expression experiment suggest that $p57^{KIP2}$ is a candidate inhibitor of intra-S phase DNA synthesis rate, capable of prolonging S phase duration in S0 cells.

Figures 3A, 3B, 3C, 3D, 3E, 3F, 3G:
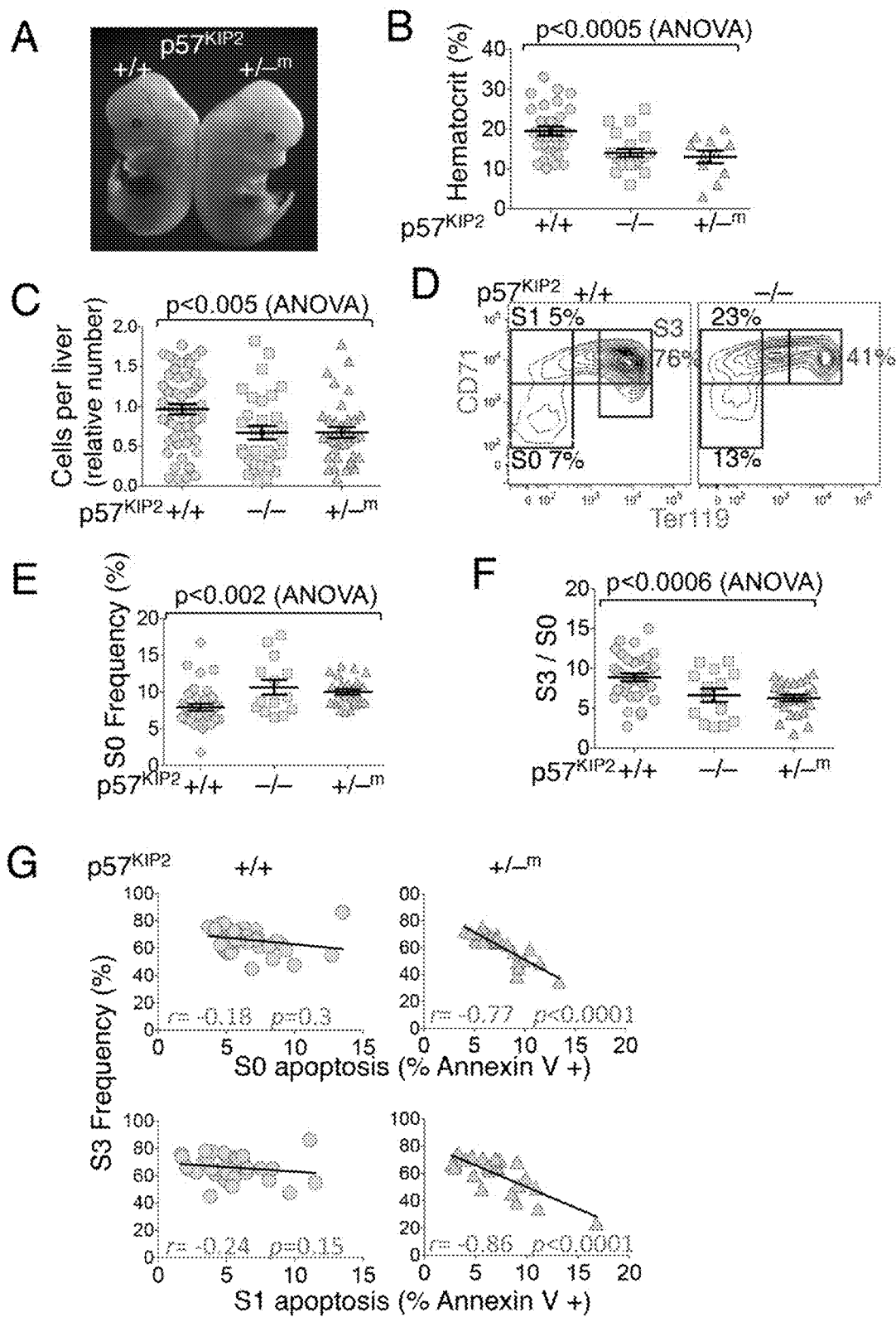

Example 1.3—$p57^{KIP2}$-Deficient Embryos are Anemic as a Result of Abnormal Erythropoiesis To test whether $p57^{KIP2}$ regulates S phase duration in erythroid progenitors, we examined embryos deleted for the cdkn1c gene, which encodes $p57^{KIP2}$ (48, 49). $p57^{KIP2}$ deficiency was previously found to result in perinatal death, associated with a variety of developmental abnormalities including abnormal abdominal muscles, intestines, kidney, adrenals and bones (48, 49). Erythropoiesis in $p57^{KIP2}$-deficient mice was not, however, examined. $p57^{KIP2}$ is a paternally imprinted gene. We examined $p57^{KIP2}$ and $p57^{KIP2}+/-^m$ (=heterozygous embryos that inherited the maternal null allele) at mid-gestation. We found that, while a proportion of the $p57^{KIP2}$—deficient embryos were morphologically abnormal, the majority had preserved gross normal morphology, enabling us to easily identify and explant the fetal liver (FIG. 3A). $p57^{KIP2}$-deficient embryos appeared paler than wild-type littermates (FIG. 3A) and were anemic (hematocrit=19.5±1.1 for wild type embryos, vs. 14.0±1.0 and 13.0±1.6 for $p57^{KIP2}-/-$ and $p57^{KIP2}+/-^m$ embryos, respectively, mean±SE, FIG. 3B). Anemia in the $p57^{KIP2}$-deficient embryos was likely the result of abnormal erythropoiesis, since these embryos had smaller fetal livers containing significantly fewer cells (FIG. 3C). Flow cytometric profiles of the fetal liver suggested abnormal erythroid differentiation (FIG. 3D-F). Thus, the ratio of S3 to S0 cells in $p57^{KIP2}$-deficient fetal livers was significantly reduced (FIG. 3D, F). Of note, the absolute number of S0 cells per fetal liver was unchanged compared with wild-type littermate embryos, since the frequency of S0 cells within the fetal liver of $p57^{KIP2}$-deficient embryos was increased in proportion to the decrease in the total number of fetal liver cells (FIG. 3C, E). The reduced S3 to S0 ratio therefore indicates a failure of S0 cells to differentiate efficiently into S3 erythroblasts. This failure is explained by increased cell death: there was a significant negative correlation between the frequency of S3 cells in the $p57^{KIP2}$-deficient fetal livers, and apoptosis of either S0 (r=−0.77, p<0.0001, FIG. 3G) or S1 cells (r=−0.86, p<0.0001; FIG. 3G). In contrast, there was no significant correlation between the number of apoptotic S0 or S1 cells and S3 frequency in wild-type littermate embryos (FIG. 3G). Taken together, these results show that $p57^{KIP2}$-deficiency causes anemia, secondary to cell death at the S0 and S1 progenitor stage, resulting in reduced number of maturing S3 erythroblasts.

Figures 4A, 4B, 4C, 4D, 4E, 4F:
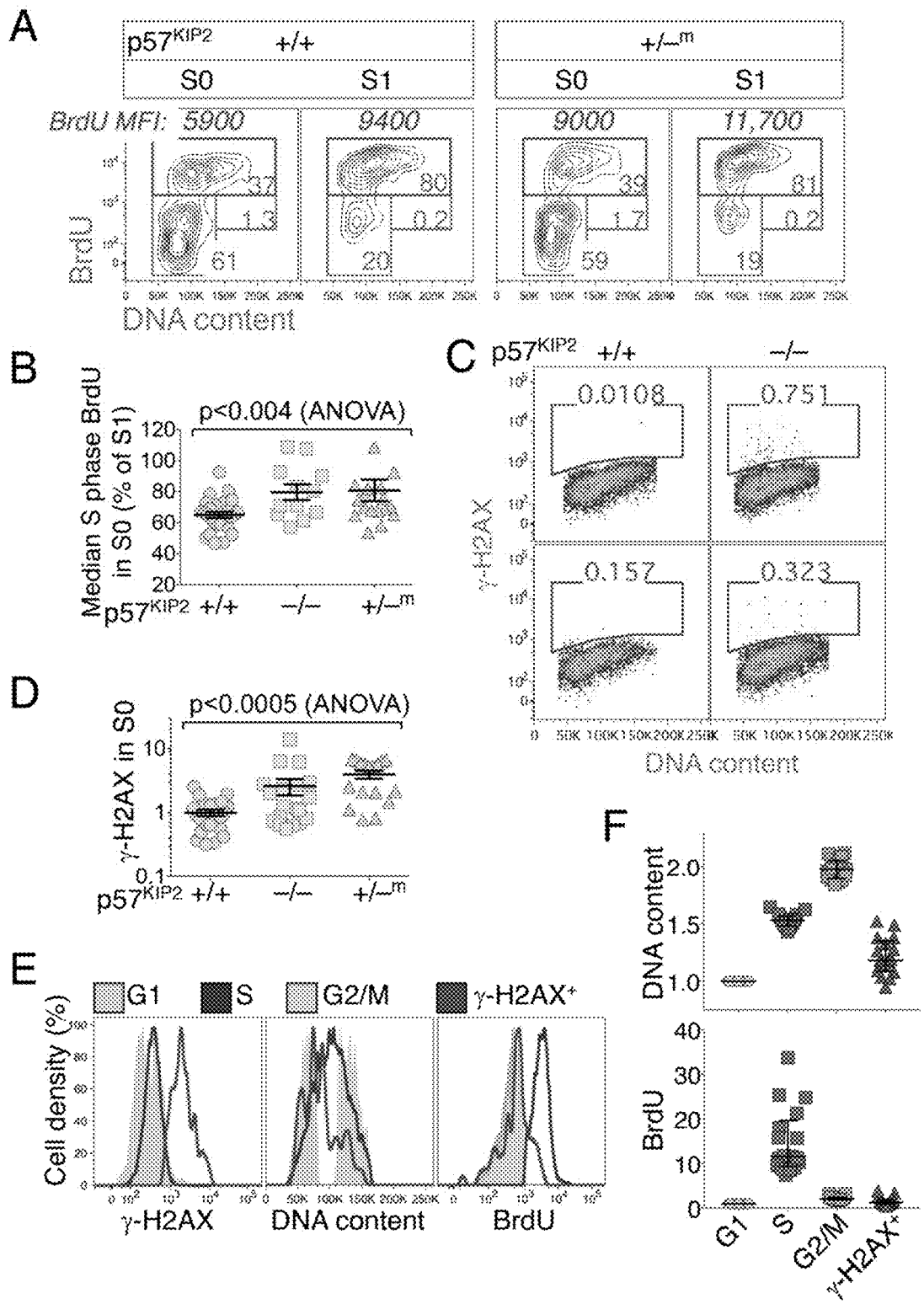

Example 1.4—Premature S Phase Shortening and DNA Damage in $p57^{KIP2}$-Deficient S0 Progenitors We examined cell cycle status in $p57^{KIP2}$-deficient fetal livers, by subjecting pregnant female mice at mid-gestation to a 30' pulse of BrdU. Fetal livers were then explanted and individually analyzed for intra-S phase DNA synthesis rate (FIG. 4A-B). In wild-type embryos, intra-S phase DNA synthesis rate in S0 cells was 65±0.02% of the peak intra-S phase DNA synthesis rate in S1 cells of the same fetal liver (mean±SE, n=29, FIG. 4A-B), in agreement with our observation of S phase shortening at the S0/S1 transition (FIG. 7C-D, FIG. 1B-E). By contrast, intra-S phase DNA synthesis rate of littermate $p57^{KIP2}$-deficient S0 cells was significantly faster, reaching 80±0.05% ($p57^{KIP2}-/-$, n=12) and 80±0.07% ($p57^{KIP2}+/-^m$, n=18) of the peak intra-S phase DNA synthesis rate of the corresponding S1 cells in each fetal liver (p<0.004, FIG. 4A-B).

The prematurely fast intra-S phase DNA synthesis rate in $p57^{KIP2}$-deficient S0 cells may have contributed to their increased apoptosis (FIG. 3G). We found a significant increase in the number of γ-H2AX positive S0 cells in freshly explanted $p57^{KIP2}$-deficient fetal livers (FIG. 4C-D). DNA content analysis of γ-H2AX-positive S0 cells in $p57^{KIP2}$-deficient fetal livers shows that they are distributed in S phase of the cycle, although fewer γ-H2AX-positive cells reach late S phase (FIGS. 4C, E-F). Thus, the DNA contents of S and G2/M phase cells in the S0 subset of each fetal liver were 153±1.2% and 198±2.2% the DNA content in G1, respectively (mean±sem for 17 $p57^{KIP2}+/-^m$ embryos); DNA content of γ-H2AX-positive cells in the same fetal livers was 121±3.6% the G1 content (FIG. 4E, F). These findings suggest that γ-H2AX-associated DNA damage occurred in S phase of the cycle, and raises the possibility that it was a consequence of the prematurely fast intra-S phase DNA synthesis rate in these cells. Of interest, we found that S phase cells that were also positive for γ-H2AX incorporated little or no BrdU, consistent with S phase slowing or arrest secondary to DNA damage and replicative stress (FIG. 4E-F).

The elevated number of γ-H2AX-positive cells in $p57^{KIP2}$-deficient embryos persisted for the remainder of erythroblast differentiation (FIG. 9A-B). Notably, wild-type S1 cells showed relatively low levels of γ-H2AX staining, suggesting that they are adapted in some way to high rates of DNA synthesis (FIG. 9B).

In summary, our analysis of $p57^{KIP2}$-deficient embryos in vivo uncovers a novel intra-S phase function for $p57^{KIP2}$, as a suppressor of global DNA synthesis rate. $p57^{KIP2}$ exerts this function in early erythroid CFUe progenitors in the S0 subset, increasing S phase duration and enhancing cell viability, at least in part by reducing replicative stress. The premature shortening of S phase in $p57^{KIP2}$-deficient S0 cells suggests that loss of $p57^{KIP2}$ is sufficient to induce S phase shortening. $p57^{KIP2}$ downregulation is therefore a likely mechanism underlying S phase shortening during the S0/S1 cell fate switch.

Example 1.5—$p57^{KIP2}$ is Essential for Self-Renewal of CFUe In Vitro

We next examined whether we could model the S phase function of $p57^{KIP2}$ in vitro. Glucocorticoids slow or arrest the differentiation of CFUe progenitors in culture, promoting extensive self-renewal instead (47, 50). Withdrawal of glucocorticoids from the culture precipitates the prompt induction of ETD and its completion within 72 h (47, 51, 52). The precise mechanism by which glucocorticoids promote self-renewal is not fully understood but several pathways have been implicated recently (53-55). Here we found that CFUe undergoing self-renewal in vitro in the presence of the synthetic glucocorticoid dexamethasone (Dex) expressed $p57^{KIP2}$ mRNA and protein (FIG. 5A-B). Withdrawal of Dex resulted in rapid induction of erythroid gene transcription, and also in a rapid (<24 hour) loss of $p57^{KIP2}$ expression (FIG. 5A-B). These changes in $p57^{KIP2}$ expression were associated with corresponding cell cycle changes: CFUe undergoing self-renewal in the presence of Dex had a slow intra-S phase DNA synthesis rate that increased abruptly with the withdrawal of Dex (FIG. 5C; in measurements taken 20 to 60 hours post Dex withdrawal, BrdU MFI increased by 74±29%, mean±sem, p=0.04). The stimulatory impact of p57$^{KIP2}$ downregulation on intra-S phase DNA synthesis rate following Dex withdrawal mirrors our observations in vivo, during the switch to ETD at the S0/S1 transition (FIG. 7C-D, FIG. 1C-E).

Next, we assessed the role of p57$^{KIP2}$ during CFUe self-renewal in vitro. We established Dex cultures from individual fetal livers of either p57$^{KIP2}$-deficient or wild-type littermate embryos. By day 6, the number of self-renewing cells in the wild-type cultures increased 50-fold. By contrast, there was no amplification of cells in cultures from p57$^{KIP2}$−/− fetal livers, suggesting a novel, essential role for p57$^{KIP2}$ during Dex-dependent self-renewal in vitro (FIGS. 5D, 10A; n=5 independent cultures from individual p57$^{KIP2}$−/− embryos and 4 cultures from wild-type littermates). p57$^{KIP2}$+/−$^m$ cultures showed an intermediate, but significantly reduced amplification compared with wild type (17 fold; FIG. 5D, 10A, n=4 independent p57$^{KIP2}$+/−$^m$ cultures and 4 cultures from wild-type littermates). The difference between p57$^{KIP2}$−/−$^m$ cultures was explained by a low level of expression of p57$^{KIP2}$ in the p57$^{KIP2}$+/−$^m$ cultures (FIG. 5E), which became evident with increasing days in culture (FIG. 10B-C). It likely represents a selective advantage for cells in which the imprinted p57$^{KIP2}$ allele was incompletely silenced, further underscoring the importance of p57$^{KIP2}$ expression to CFUe self-renewal. Of note, there was no compensatory upregulation of either p21$^{CIP1}$ or p27$^{KIP2}$ in Dex cultures of p57$^{KIP2}$ deficient cells (FIG. 10B-C).

The failure of p57$^{KIP2}$-deficient CFUe to undergo self-renewal was associated with a substantial increase in cell death (FIG. 11). The intra-S phase DNA synthesis rate in cultures of p57$^{KIP2}$-deficient CFUe was increased compared with matching wild-type cultures (FIG. 5F). Further, consistent with our observations in vivo, the frequency of γ-H2AX-positive cells was also elevated (FIG. 5G). DNA damage associated with faster replication is therefore a likely cause of cell death in p57$^{KIP2}$-deficient p57$^{KIP2}$ CFUe in vitro, analogous to the death of S0 CFUe in vivo (FIGS. 3G, 4D). DNA damage leading to cell death may potentially explain the apparently paradoxical requirement for a CDK inhibitor during self-renewal and population growth. We were able to restore self-renewal potential to the p57$^{KIP2}$−/− CFUe cultures by transducing the p57$^{KIP2}$ cells with retroviral vectors expressing p57$^{KIP2}$ (FIG. 5H), indicating that this effect is cell autonomous.

In summary, we successfully modeled in vitro the novel functions that we first uncovered for p57$^{KIP2}$ during S phase of CFUe progenitors in vivo. Our results show that p57$^{KIP2}$ is expressed in self-renewing CFUe both in vitro and in vivo, where it slows intra-S phase DNA synthesis rate, protects cells from DNA damage during DNA replication, and promotes cell viability. The switch to differentiation both in vivo and in vitro entails rapid downregulation of p57$^{KIP2}$, with ensuing increased intra-S phase DNA synthesis rate and S phase shortening.

Example 1.6—p57$^{KIP2}$-Mediated CDK Inhibition Underlies its S Phase Functions The Cip/Kip family member p21$^{CIP1}$ interacts with PCNA, inhibiting S phase DNA synthesis during the DNA damage response (56, 57). Murine p57$^{KIP2}$, however, lacks a PCNA interaction domain (58). To investigate the mechanisms underlying p57$^{KIP2}$-mediated regulation of S phase duration, we generated two distinct p57$^{KIP2}$ point mutants within its conserved CDK binding motif, p57W50G and p57F52A/F54A (59, 60). Neither of these mutants, when expressed in S0 cells, significantly inhibited intra-S phase DNA synthesis rate, while cells transduced in parallel with similar levels of wild-type p57$^{KIP2}$ successfully slowed or arrested S phase (FIG. 12A). This result suggests that CDK binding by p57$^{KIP2}$, and the likely ensuing CDK inhibition, mediates its intra-S phase slowing of DNA synthesis.

We also investigated whether CDK inhibition could underlie the essential role that p57$^{KIP2}$ plays in maintaining the viability of self-renewing CFUe. We treated p57$^{KIP2}$-deficient fetal liver CFUe with the CDK inhibitor roscovitine, which preferentially inhibits S phase cyclin/CDK activity (61). We found that a low concentration of roscovitine (0.5 µM) successfully rescued Dex-dependent self-renewal and expansion of p57$^{KIP2}$-deficient CFUe while having little effect on the normal expansion of CFUe cultures derived from wild-type littermates (FIG. 5I). Population growth in cultures containing roscovitine was indeed the result of CFUe self-renewal, as shown by their preserved CFUe colony potential (FIG. 12B).

We also found that addition of roscovitine enhanced the amplification of wild-type CFU-e (FIGS. 5I-J). In three independent experiments, wild-type cells growing in roscovitine were amplified an average of 1.92±0.43 fold more than wild-type cells without treatment.

Thus, paradoxically, inhibition of CDK activity promotes CFUe viability and self-renewal potential, in agreement with the essential requirement for p57$^{KIP2}$ for these functions. Taken together, these results show that CDK inhibition is the likely mechanism through which p57$^{KIP2}$ both suppresses intra-S phase DNA synthesis rate and promotes the viability and self-renewal potential of early erythroid progenitors.

Example 1.7 Faster Replication Forks Underlie S Phase Shortening at the S0/S1 Transition CDK activity is required for the firing of origins of replication (62, 63). Suppression of CDK activity, leading to reduced origin firing, was recently implicated in the lengthening of S phase at the midblastula transition (64). Given the role of p57$^{KIP2}$ in both CDK inhibition and in slowing intra-S phase DNA synthesis, we sought to determine whether there were associated changes in origin firing frequency. To this end, we employed DNA combing, a single-molecule DNA fiber approach that allows effects on origin firing and fork progression to be deconvoluted (65, 66). We explanted littermate wild-type and p57$^{KIP2}$+/− in fetal livers at mid-gestation, allowing fetal liver cells to recover for 4 hours at 37° C. We then pulsed the cells for 10 minutes with 25 µM of the deoxynucleoside analog iododeoxyuridine (IdU). This was followed by a pulse of an 8-fold higher concentration of a second deoxynucleoside analog, chlorodeoxyuridine (CldU), in order to abruptly switch from IdU to CldU and allow determination of fork directionality (FIG. 6A). The fetal liver cells were then placed on ice, and S0 and S1 cells were sorted by flow cytometry. Genomic DNA was combed from each of the wild-type and p57$^{KIP2}$+/−$^m$ S0 and S1 populations, by isolating and stretching on glass coverslips. Combed DNA was stained for IdU (green fluorescence) and CldU (red fluorescence) incorporation and for single-stranded DNA (blue fluorescence, FIG. 6B). We measured distances between adjacent origins, and the speed of forks during the IdU pulse (FIG. 6B). Only forks that moved throughout the IdU pulse, as reflected by immediately adjacent and consecutive blue, green and red/yellow tracks, were included in the analysis of fork speed (FIG. 6B; of note, the beginning of CldU incorporation into the replication bubble is recognized at the point of first appearance of red fluorescence, whether or not green IdU fluorescence is simultaneously also present, together labeling as yellow; this is since intracellular IdU is still present at the onset of the second pulse. Where all three antibodies label DNA, the resulting color is white.). Approximately 20 Mb were examined for each of wild type and $p57^{KIP2}+/-^m$ S0 and S1 DNA, with an average fiber length of 1 Mb for each of the four samples (FIG. 13A). We found no significant difference in inter-origin distance between wild-type S0 and S1 cells, or between wild-type and corresponding $p57^{KIP2}+/-^m$ cells (FIG. 6C, FIG. 13B). Remarkably, fork speed in wild-type S1 cells was increased 56% compared to wild-type S0 [2.43±0.11 vs. 1.56±0.08 kb/min in S1 and S0 respectively, mean±SE, $p<10^{-8}$). A similar result was obtained in an independent experiment in which S0 and S1 cells from a different inbred wild-type mouse strain (Balb/C) were similarly analyzed (FIG. 14A-B). Therefore, surprisingly, S phase shortening in S1 in wild type cells is the result of a significant global increase in fork processivity, and does not reflect a change in origin firing efficiency.

Consistent with our earlier result showing premature S phase shortening in $p57^{KIP2}$ deficient embryos (FIG. 4A-B), we found a 35% increase in fork speed of $p57^{KIP2}+/-^m$ S0 cells compared with wild-type S0 cells (2.11±0.09 vs. 1.56±0.08 kb/min, respectively, $p=10^{-5}$, FIG. 6C-E). Finally, there was a further 30% increase in fork speed with the transition from S0 to S1 in $p57^{KIP2}+/-^m$ fetal liver (FIG. 6C-E, $p=0.0004$). Thus, $p57^{KIP2}$ normally restrains S0 DNA synthesis rate by inhibiting fork processivity, as indicated by the elevated fork speed in $p57^{KIP2}+/-^m$ S0 cells. Although fork speed in $p57^{KIP2}+/-^m$ S0 cells is substantially faster than in wild type S0, it is nevertheless still somewhat slower than fork speeds seen in S1 of the same fetal livers (FIGS. 6C,6E).

Taken together, these findings suggest that S phase shortening at the S0 to S1 transition in wild type cells is the result of downregulation of $p57^{KIP2}$, which restrains intra-S phase DNA synthesis rate in S0 cells by globally suppressing the processivity of replication forks.

We also used DNA combing to analyze the underlying mechanism of $p57^{KIP2}$-mediated slowing of DNA synthesis rate during Dex-dependent CFUe self-renewal in vitro. In agreement with our findings in vivo, $p57^{KIP2}$ deficiency resulted in significantly faster replication forks, with no significant change in inter-origin distance (FIG. 14C).

Example 2. Cell Cycle Regulation During the Self-Renewal Phase of Erythroid Progenitors We previously showed that the transition from self-renewal to erythroid terminal differentiation is synchronized with, and dependent on, S phase of the cycle[23]. We found that erythroid fetal liver CFU-e progenitors express an endogenous CDK inhibitor, $p57^{KIP2}$ CDK inhibition by $p57^{KIP2}$ in these cells slows down S phase of the cycle and is essential for their self-renewal. The transition from self-renewal to erythroid terminal differentiation is marked by a rapid decline in $p57^{KIP2}$ expression and in S phase shortening. As shown herein, drugs that inhibit the S-phase CDK, CDK2, could enhance endogenous CDK2 inhibition, slow down S phase, and thereby delay terminal differentiation, promoting self-renewal instead.

Our initial findings were explored in the mouse fetal liver. This example generalizes these findings and shows that they also apply to bone-marrow progenitors. Briefly, we used single-cell RNA sequencing, new computational analytical tools, and a new flow-cytometric strategy, to delineate the entire erythroid trajectory in mouse bone marrow and fetal liver. This analysis showed that the transition from self-renewal to terminal differentiation is synchronized with a unique cell cycle S phase at the single cell transcriptome level in both the fetal liver and the adult bone marrow. We also showed functional interdependence between S phase and the switch to differentiation in adult bone-marrow progenitors.

This example also shows that, in addition to a long S phase, the self-renewal phase requires a long G1; progressive G1 shortening precedes the switch to terminal differentiation. Taken together, it is likely that CDK inhibition prolongs both G1 and S phase and hence delays the switch to terminal differentiation. The prolonged self-renewal phase results in a larger pool of early, CFU-e progenitors.

Figures 16A, 16B, 16C, 16D:
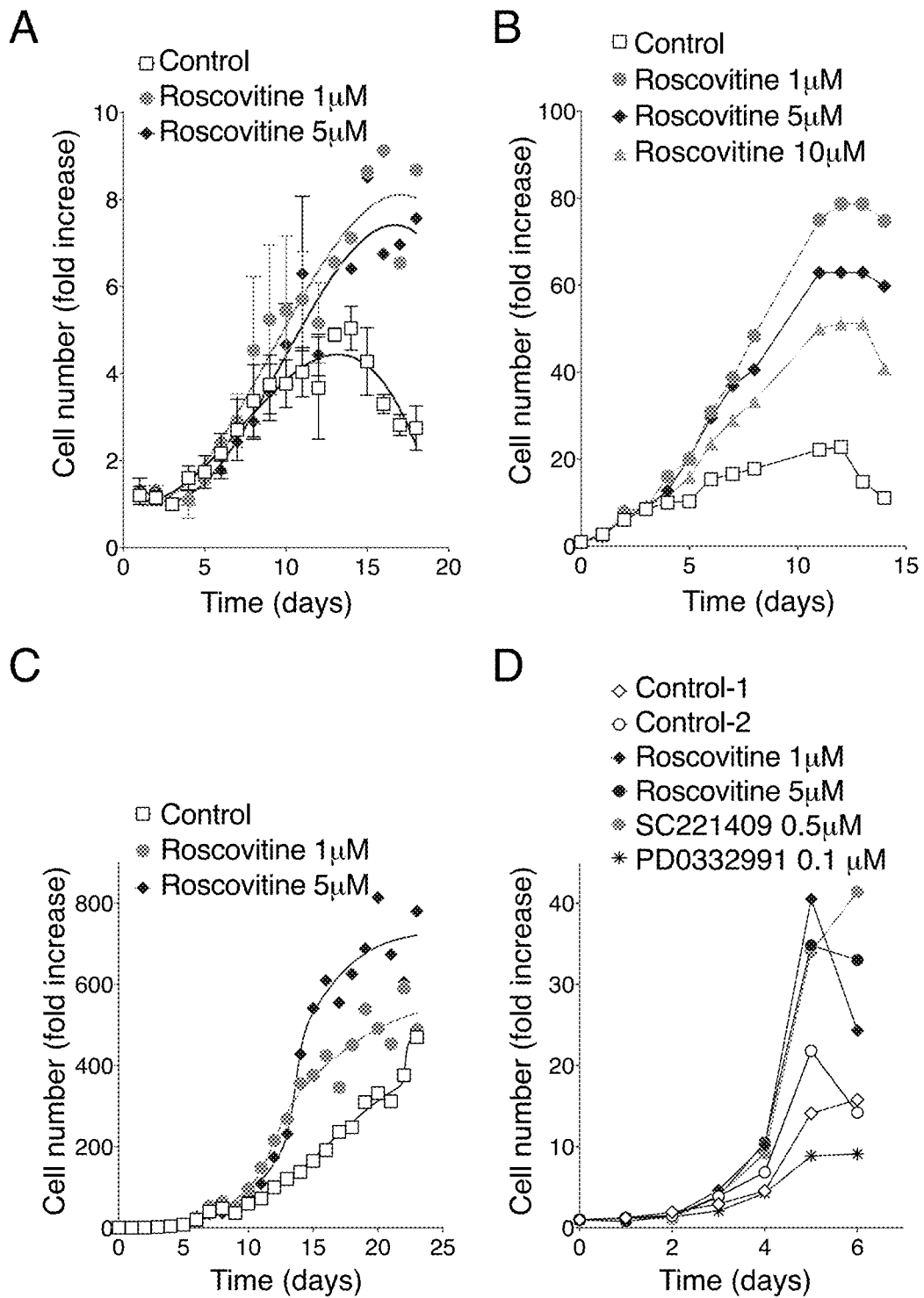

Example 2.1—CDK Inhibition by Roscovitine Doubles the Self-Renewal Potential of Human and Mouse CFU-e Erythroid Progenitors In Vitro We cultured hematopoietic tissue cells from either mouse adult bone marrow, mouse fetal liver (mid-gestation, embryonic day 13.5), or human adult bone marrow (StemCell Technologies, Vancouver, Canada), under conditions that facilitate self-renewal of colony-forming-unit-erythroid (CFU-e), in which the following are added to the culture medium: erythropoietin (Epo, 2 Units/ml), Stem Cell Factor (SCF, 100 ng/ml), Insulin-like Growth Factor 1 (IGF1, 40 ng/ml) and dexamethasone (Dex, 1 µM). Control cultures contained no other specialized additives; parallel cultures had, in addition, the CDK inhibitor roscovitine (1, 5 or 10 µM) (Pippin et al., J Clin Invest 100, 2512-2520 (1997); Meijer et al., European Journal of Biochemistry 243, 527-536 (1997)). FIGS. 16A-16D shows that addition of roscovitine results in a prolongation of the period in which amplification of erythroid cells is possible, and in attaining a higher cell number, particularly during the latter half of the culture period. Thus, in the presence of roscovitine, in data pooled from two independent experiments (FIG. 16A), human bone-marrow cultures reached peak amplification of cell number by 9-fold on day 16, compared with a peak of 5-fold amplification on day 14 in control cultures ($p=0.027$ when comparing the roscovitine with control cultures for the entire 18 day culture period; $p=0.00001$ when comparing the cultures between days 8 and 18 only; two-tailed paired t test, unequal variance). Similarly, significantly higher cell numbers were obtained in cultures of mouse fetal liver and mouse adult bone marrow to which roscovitine was added (FIGS. 16B-16D).

Liquid cultures of erythroid cells under these conditions often contain mixtures of cells at various differentiation stages, spanning the BFU-e, CFU-e, proerythroblast and erythroblast stages. In order to determine whether the increased cell number in fact corresponds to an increase in the early progenitor cells with the potential to form CFU-e colonies, we plated cells from each culture in semi-solid medium, and counted the resulting CFU-e colonies 3 days later. Cells taken on day 11 of human bone marrow cultures to which roscovitine was added gave rise to significantly more CFU-e colonies than controls: there was a 3.9-fold increase in the absolute number of CFU-e progenitors over the number seen in control cultures with the addition of 1 µM of roscovitine (p=0.0002, two-tailed t test, unequal variance), and a 4.5-fold increase relative to control with 5 µM of roscovitine (p=0.001) (FIG. 17A). In a similar experiment with mouse bone-marrow, on day 5 of culture, we measured a 62% increase in absolute CFU-e numbers relative to control cultures on the same day, with the addition of 1 µM of roscovitine (p=0.0003), and a 40% increase with 5 µM of roscovitine (p=0.03)(FIG. 17B).

Example 2.2—Amplification of CFU-e Progenitors by Inhibitors that Target CDK2, but not CDK4 or CDK6

Roscovitine inhibits CDK2 as well as CDK5. To determine with more precision the type of CDK inhibition that enhances CFU-e self-renewal, we tested two additional CDK inhibitor drugs: SC-221409 (Abcam, ab145053), a selective and potent CDK2 inhibitor ($IC_{50}$=60 nM); and PD0332991 (Abcam, ab218118), a potent and selective inhibitor of CDK4 ($IC_{50}$=11 nM) and CDK6 ($IC_{50}$=16 nM). We added SC-221409 to the self-renewal cultures of mouse bone-marrow erythroid progenitors, at 0.5 µM, and found a significant increase, when compared with control cultures, in both the amplification of erythroid cell number (FIG. 16D) and in the absolute number of CFU-e progenitors as judged by colony formation assays (FIG. 17B), compared with control cultures. These effects were numerically similar to those found with roscovitine in the same experiments. By contrast, the addition of PD0332991 (0.1 µM) had either no significant effect or an inhibitory effect compared with controls, in the same experiments. The doses chosen for all these inhibitors were approximately 5 times the IC50 for each drug. We conclude that the target for drug inhibition required for enhancement of erythroid progenitor self-renewal is CDK2, and not CDK4 or CDK6.

Example 3.3—Flow-Cytometric Evidence that CDK2 Inhibition Slows Down Erythroid Differentiation and Promotes Self-Renewal of Early Progenitors We examined cells in the self-renewing cultures using flow-cytometry. Cell surface markers CD71 and Ter119 denote the differentiation stage of erythroid progenitors and precursors in mouse hematopoietic tissue[81,41]. We found that treatment with roscovitine skews the cells in mouse bone marrow cultures in favor of less differentiated cells, so that very few of the cells in the culture (6%) expressed Ter119, a marker of terminally differentiating erythroblasts that is absent in self-renewing CFU-e progenitors (FIG. 18A). By contrast, control cultures contained a substantial fraction (35%) of Ter119+ cells. Cell cycle analysis showed that, as expected, roscovitine treatment resulted in fewer S phase cells, and that the speed of S phase, as measured by the rate of BrdU incorporation, was substantially slower.

Flow cytometric analysis of human bone marrow cultures similarly indicated that roscovitine treatment skewed the cultures in favor of less differentiated, earlier progenitors, as indicated by the distribution of cell surface markers CD36 and glycophorin A; in particular, fewer cells are glycophorin A positive (FIG. 18B).

REFERENCES

1. S. Lim, P. Kaldis, Cdks, cyclins and CKIs: roles beyond cell cycle regulation. *Development* 140, 3079-3093 (2013).
2. W. Gu et al., Interaction of myogenic factors and the retinoblastoma protein mediates muscle cell commitment and differentiation. *Cell* 72, 309-324 (1993).
3. J. J. Bird et al., Helper T Cell Differentiation Is Controlled by the Cell Cycle. *Immunity* 9, 229-237 (1998).
4. L. Zhu, A. I. Skoultchi, Coordinating cell proliferation and differentiation. *Curr Opin Genet Dev* 11, 91-97 (2001).
5. J. Cai, M. L. Weiss, M. S. Rao, In search of "stemness". *Exp Hematol* 32, 585-598 (2004).
6. K. A. Gonzales et al., Deterministic Restriction on Pluripotent State Dissolution by Cell-Cycle Pathways. *Cell* 162, 564-579 (2015).
7. S. Dalton, Linking the Cell Cycle to Cell Fate Decisions. *Trends Cell Biol* 25, 592-600 (2015).
8. H. Weintraub, Assembly of an active chromatin structure during replication. *Nucleic Acids Res* 7, 781-792 (1979).
9. A. P. Wolffe, Implications of DNA replication for eukaryotic gene expression. *J Cell Sci* 99 (Pt 2), 201-206 (1991).
10. S. Henikoff, Nucleosome destabilization in the epigenetic regulation of gene expression. *Nat Rev Genet* 9, 15-26 (2008).
11. C. P. Chiu, H. M. Blau, Reprogramming cell differentiation in the absence of DNA synthesis. *Cell* 37, 879-887 (1984).
12. V. Hartenstein, J. W. Posakony, Sensillum development in the absence of cell division: the sensillum phenotype of the *Drosophila* mutant string. *Dev Biol* 138, 147-158 (1990).
13. B. A. Edgar, P. H. O'Farrell, The three postblastoderm cell cycles of *Drosophila* embryogenesis are regulated in G2 by string. *Cell* 62, 469-480 (1990).
14. W. A. Harris, V. Hartenstein, Neuronal determination without cell division in *Xenopus* embryos. *Neuron* 6, 499-515 (1991).
15. J. C. de Nooij, I. K. Hariharan, Uncoupling cell fate determination from patterned cell division in the *Drosophila* eye. *Science* 270, 983-985 (1995).
16. A. M. Miller, K. A. Nasmyth, Role of DNA replication in the repression of silent mating type loci in yeast. *Nature* 312, 247-251 (1984).
17. O. M. Aparicio, D. E. Gottschling, Overcoming telomeric silencing: a trans-activator competes to establish gene expression in a cell cycle-dependent way. *Genes Dev* 8, 1133-1146 (1994).
18. L. G. Edgar, J. D. McGhee, DNA synthesis and the control of embryonic gene expression in C. elegans. *Cell* 53, 589-599 (1988).
19. K. Weigmann, C. F. Lehner, Cell fate specification by even-skipped expression in the Drosophila nervous system is coupled to cell cycle progression. *Development* 121, 3713-3721 (1995).
20. S. Forlani, C. Bonnerot, S. Capgras, J. F. Nicolas, Relief of a repressed gene expression state in the mouse 1-cell embryo requires DNA replication. *Development* 125, 3153-3166 (1998).
21. V. Ambros, Cell cycle-dependent sequencing of cell fate decisions in *Caenorhabditis elegans* vulva precursor cells. *Development* 126, 1947-1956 (1999).
22. D. Fisher, M. Mechali, Vertebrate HoxB gene expression requires DNA replication. *Embo J* 22, 3737-3748 (2003).
23. R. Pop et al., A key commitment step in erythropoiesis is synchronized with the cell cycle clock through mutual inhibition between PU.1 and S-phase progression. *PLoS Biol* 8, (2010).
24. C. J. Gregory, A. D. Tepperman, E. A. McCulloch, J. E. Till, Erythropoietic progenitors capable of colony formation in culture: response of normal and genetically anemic W-W-V mice to manipulations of the erythron. *J Cell Physiol* 84, 1-12 (1974).
25. H. Hara, M. Ogawa, Erthropoietic precursors in mice with phenylhydrazine-induced anemia. *Am J Hematol* 1, 453-458 (1976).
26. A. B. Cantor, S. H. Orkin, Transcriptional regulation of erythropoiesis: an affair involving multiple partners. *Oncogene* 21, 3368-3376 (2002).
27. S. N. Wontakal et al., A core erythroid transcriptional network is repressed by a master regulator of myelo-lymphoid differentiation. *Proc Natl Acad Sci USA* 109, 3832-3837 (2012).
28. J. R. Shearstone et al., Global DNA demethylation during mouse erythropoiesis in vivo. *Science* 334, 799-802 (2011).
29. A. Spradling, T. Orr-Weaver, Regulation of DNA replication during Drosophila development. *Annu Rev Genet* 21, 373-403 (1987).
30. J. Nordman, T. L. Orr-Weaver, Regulation of DNA replication during development. *Development* 139, 455-464 (2012).
31. V. E. Foe, Mitotic domains reveal early commitment of cells in Drosophila embryos. *Development* 107, 1-22 (1989).
32. R. J. Duronio, Developing S-phase control. *Genes Dev* 26, 746-750 (2012).
33. S. L. McKnight, 0. L. Miller, Jr., Electron microscopic analysis of chromatin replication in the cellular blastoderm Drosophila melanogaster embryo. *Cell* 12, 795-804 (1977).
34. M. H. Snow, D. Bennett, Gastrulation in the mouse: assessment of cell populations in the epiblast of tw18/tw18 embryos. *J Embryol Exp Morphol* 47, 39-52 (1978).
35. A. Mac Auley, Z. Werb, P. E. Mirkes, Characterization of the unusually rapid cell cycles during rat gastrulation. *Development* 117, 873-883 (1993).
36. P. H. O'Farrell, J. Stumpff, T. T. Su, Embryonic cleavage cycles: how is a mouse like a fly? *Curr Biol* 14, R35-45 (2004).
37. S. Matsuoka et al., p57KIP2, a structurally distinct member of the p21CIP1 Cdk inhibitor family, is a candidate tumor suppressor gene. *Genes Dev* 9, 650-662 (1995).
38. M. H. Lee, I. Reynisdottir, J. Massague, Cloning of p57KIP2, a cyclin-dependent kinase inhibitor with unique domain structure and tissue distribution. *Genes Dev* 9, 639-649 (1995).
39. I. S. Pateras, K. Apostolopoulou, K. Niforou, A. Kotsinas, V. G. Gorgoulis, p57KIP2: "Kip"ing the cell under control. *Mol Cancer Res* 7, 1902-1919 (2009).
40. A. Besson, S. F. Dowdy, J. M. Roberts, CDK inhibitors: cell cycle regulators and beyond. *Dev Cell* 14, 159-169 (2008).
41. M. Socolovsky et al., Ineffective erythropoiesis in Stat5a(−/−)5b(−/−) mice due to decreased survival of early erythroblasts. *Blood* 98, 3261-3273. (2001).
42. J. Zhang, M. Socolovsky, A. W. Gross, H. F. Lodish, Role of Ras signaling in erythroid differentiation of mouse fetal liver cells: functional analysis by a flow cytometry-based novel culture system. *Blood* 102, 3938-3946 (2003).
43. R. Scully et al., Dynamic changes of BRCA1 subnuclear location and phosphorylation state are initiated by DNA damage. *Cell* 90, 425-435 (1997).
44. X. Q. Ge, D. A. Jackson, J. J. Blow, Dormant origins licensed by excess Mcm2-7 are required for human cells to survive replicative stress. *Genes Dev* 21, 3331-3341 (2007).
45. F. C. Monette, J. LoBue, A. S. Gordon, P. Alexander, Jr., P. C. Chan, Erythropoiesis in the rat: differential rates of DNA synthesis and cell proliferation. *Science* 162, 1132-1134 (1968).
46. B. Martynoga, H. Morrison, D. J. Price, J. O. Mason, Foxg1 is required for specification of ventral telencephalon and region-specific regulation of dorsal telencephalic precursor proliferation and apoptosis. *Dev Biol* 283, 113-127 (2005).
47. M. von Lindern et al., The glucocorticoid receptor cooperates with the erythropoietin receptor and c-Kit to enhance and sustain proliferation of erythroid progenitors in vitro. *Blood* 94, 550-559 (1999).
48. P. Zhang et al., Altered cell differentiation and proliferation in mice lacking p57KIP2 indicates a role in Beckwith-Wiedemann syndrome. *Nature* 387, 151-158 (1997).
49. Y. Yan, J. Frisen, M. H. Lee, J. Massague, M. Barbacid, Ablation of the CDK inhibitor p57Kip2 results in increased apoptosis and delayed differentiation during mouse development. *Genes Dev* 11, 973-983 (1997).
50. A. Bauer et al., The glucocorticoid receptor is required for stress erythropoiesis. *Genes Dev* 13, 2996-3002 (1999).
51. S. J. England, K. E. McGrath, J. M. Frame, J. Palis, Immature erythroblasts with extensive ex vivo self-renewal capacity emerge from the early mammalian fetus. *Blood* 117, 2708-2717 (2011).
52. A. R. Migliaccio, C. Whitsett, T. Papayannopoulou, M. Sadelain, The potential of stem cells as an in vitro source of red blood cells for transfusion. *Cell Stem Cell* 10, 115-119 (2012).
53. H.-Y. Lee et al., PPAR-[agr] and glucocorticoid receptor synergize to promote erythroid progenitor self-renewal. *Nature* 522, 474-477 (2015).
54. L. Zhang et al., ZFP36L2 is required for self-renewal of early burst-forming unit erythroid progenitors. *Nature* 499, 92-96 (2013).
55. J. Flygare, V. Rayon Estrada, C. Shin, S. Gupta, H. F. Lodish, HIF1alpha synergizes with glucocorticoids to promote BFU-E progenitor self-renewal. *Blood* 117, 3435-3444 (2011).
56. H. Flores-Rozas et al., Cdk-interacting protein 1 directly binds with proliferating cell nuclear antigen and inhibits DNA replication catalyzed by the DNA polymerase delta holoenzyme. *Proc Natl Acad Sci USA* 91, 8655-8659 (1994).
57. S. Waga, G. J. Hannon, D. Beach, B. Stillman, The p21 inhibitor of cyclin-dependent kinases controls DNA replication by interaction with PCNA. *Nature* 369, 574-578 (1994).
58. H. Watanabe et al., Suppression of cell transformation by the cyclin-dependent kinase inhibitor p57KIP2 requires binding to proliferating cell nuclear antigen. *Proc Natl Acad Sci USA* 95, 1392-1397 (1998).
59. Y. Hashimoto et al., Critical role for the 310 helix region of p57(Kip2) in cyclin-dependent kinase 2 inhibition and growth suppression. *J Biol Chem* 273, 16544-16550 (1998).
60. J. Vlach, S. Hennecke, B. Amati, Phosphorylation-dependent degradation of the cyclin-dependent kinase inhibitor p27. *EMBO J* 16, 5334-5344 (1997).

61. L. Meijer et al., Biochemical and Cellular Effects of Roscovitine, a Potent and Selective Inhibitor of the Cyclin-Dependent Kinases cdc2, cdk2 and cdk5. *European Journal of Biochemistry* 243, 527-536 (1997).
62. S. Tanaka et al., CDK-dependent phosphorylation of Sld2 and Sld3 initiates DNA replication in budding yeast. *Nature* 445, 328-332 (2007).
63. P. Zegerman, J. F. Diffley, Phosphorylation of Sld2 and Sld3 by cyclin-dependent kinases promotes DNA replication in budding yeast. *Nature* 445, 281-285 (2007).
64. J. A. Farrell, A. W. Shermoen, K. Yuan, P. H. O'Farrell, Embryonic onset of late replication requires Cdc25 down-regulation. *Genes Dev* 26, 714-725 (2012).
65. A. Bensimon et al., Alignment and sensitive detection of DNA by a moving interface. *Science* 265, 2096-2098 (1994).
66. J. N. Bianco et al., Analysis of DNA replication profiles in budding yeast and mammalian cells using DNA combing. *Methods* 57, 149-157 (2012).
67. A. Goren, H. Cedar, Replicating by the clock. *Nat Rev Mot Cell Biol* 4, 25-32 (2003).
68. I. Hiratani, S. Takebayashi, J. Lu, D. M. Gilbert, Replication timing and transcriptional control: beyond cause and effect—part II. *Curr Opin Genet Dev* 19, 142-149 (2009).
69. R. S. Hansen et al., Sequencing newly replicated DNA reveals widespread plasticity in human replication timing. *Proc Natl Acad Sci USA* 107, 139-144 (2010).
70. M. K. Zeman, K. A. Cimprich, Causes and consequences of replication stress. *Nat Cell Biol* 16, 2-9 (2014).
71. Rebecca M. Jones, E. Petermann, Replication fork dynamics and the DNA damage response. *Biochemical Journal* 443, 13-26 (2012).
72. Kara A. Nyberg, Rhett J. Michelson, a. Charles W. Putnam, T. A. Weinert, Toward Maintaining the Genome: DNA Damage and Replication Checkpoints. *Annual Review of Genetics* 36, 617-656 (2002).
73. C. Conti, J. Seiler, Y. Pommier, The Mammalian DNA Replication Elongation Checkpoint: Implication of Chk1 and Relationship with Origin Firing as Determined by Single DNA Molecule and Single Cell Analyses. *Cell Cycle* 6, 2760-2767 (2007).
74. A. D. Gitlin et al., HUMORAL IMMUNITY. T cell help controls the speed of the cell cycle in germinal center B cells. *Science* 349, 643-646 (2015).
75. R. Li, S. Waga, G. J. Hannon, D. Beach, B. Stillman, Differential effects by the p21 CDK inhibitor on PCNA-dependent DNA replication and repair. *Nature* 371, 534-537 (1994).
76. W. W. K. Lam et al., Analysis of germline CDKN1C (p57KIP2) mutations in familial and sporadic Beckwith-Wiedemann syndrome (BWS) provides a novel genotype-phenotype correlation. *Journal of Medical Genetics* 36, 518-523 (1999).
77. V. Romanelli et al., CDKN1C (p57Kip2) analysis in Beckwith Wiedemann syndrome (BWS) patients: Genotypephenotype correlations, novel mutations, and polymorphisms. *American Journal of Medical Genetics* Part A 152A, 1390-1397 (2010).
78. P. Zou et al., p57(Kip2) and p27(Kip1) cooperate to maintain hematopoietic stem cell quiescence through interactions with Hsc70. *Cell Stem Cell* 9, 247-261 (2011).
79. A. Matsumoto et al., p57 is required for quiescence and maintenance of adult hematopoietic stem cells. *Cell Stem Cell* 9, 262-271 (2011).
80. G. Migliaccio et al., In vitro mass production of human erythroid cells from the blood of normal donors and of thalassemic patients. *Blood Cells Mot Dis* 28, 169-180 (2002).
81. M. Koulnis et al., Identification and Analysis of Mouse Erythroid Progenitors using the CD71/TER119 Flow-cytometric Assay. *J Vis Exp*, (2011).
82. M. von Lindern, U. Schmidt, H. Beug, Control of erythropoiesis by erythropoietin and stem cell factor: a novel role for Bruton's tyrosine kinase. *Cell Cycle* 3, 876-879 (2004).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of providing a population of early erythroid progenitor cells, the method comprising:
   i) providing a starting population of human cells comprising mononuclear cells from cord blood, peripheral blood, bone marrow or other hematopoietic tissues, and
   ii) maintaining the starting population in the presence of a culture medium comprising a Cyclin-Dependent Kinase 2 (CDK2) inhibitor, erythropoietin, Stem Cell Factor (SCF), Insulin-like Growth Factor 1 (IGF1), and a glucocorticoid for at least 10 days,
   wherein the CDK2 inhibitor increases proliferation of the early erythroid progenitor cells as compared to a population of early erythroid progenitor cells in a control culture in the absence of the CDK2 inhibitor, thereby expanding the population of the early erythroid progenitor cells, wherein the CDK2 inhibitor is 1-5 µM roscovitine.

2. The method of claim 1, wherein the early erythroid progenitor cells are CFU-e cells.

3. The method of claim 1, wherein the starting population comprises Kit+, or Lin– cells.

4. The method of claim 3, wherein the starting population has been enriched for Kit+, or Lin– cells.

5. The method of claim 1, wherein the glucocorticoid is hydrocortisone or dexamethasone.

6. The method of claim 1, wherein the starting population is maintained in the culture medium for at least 11 days.

* * * * *

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: p57W50G PCR primer 1

<400> SEQUENCE: 1
ccagaaccgc ggggacttca acttcc                                        26

<210> SEQ ID NO 2
<211> LENGTH: 18
<212> TYPE: DNA
<213> ORGANISM: Artificial Sequence
<220> FEATURE:
<223> OTHER INFORMATION: p57W50G PCR primer 2

<400> SEQUENCE: 2
```

```
tcctcggcgt tcagctcg                                                      18

<210> SEQ ID NO 3
<211> LENGTH: 23
<212> TYPE: DNA
<213> ORGANISM: Artificial Sequence
<220> FEATURE:
<223> OTHER INFORMATION: p57F52A/F54A PCR primer 1

<400> SEQUENCE: 3
cgcccagcag gatgtgcctc ttc                                                23

<210> SEQ ID NO 4
<211> LENGTH: 23
<212> TYPE: DNA
<213> ORGANISM: Artificial Sequence
<220> FEATURE:
<223> OTHER INFORMATION: p57F52A/F54A PCR primer 2

<400> SEQUENCE: 4
ttggcgtccc agcggttctg gtc                                                23
```